United States Patent
Fan et al.

(10) Patent No.: US 9,341,604 B2
(45) Date of Patent: May 17, 2016

(54) DEVICES AND METHODS FOR ADAPTIVE MICRO-GAS CHROMATOGRAPHY

(71) Applicant: THE REGENTS OF THE UNIVERSITY OF MICHIGAN, Ann Arbor, MI (US)

(72) Inventors: Xudong Fan, Saline, MI (US); Yogesh B. Gianchandani, Ann Arbor, MI (US); Jing Liu, Ann Arbor, MI (US)

(73) Assignee: The Regents Of The University Of Michigan, Ann Arbor, MI (US)

(*) Notice: Subject to any disclaimer, the term of this patent is extended or adjusted under 35 U.S.C. 154(b) by 63 days.

(21) Appl. No.: 14/357,157

(22) PCT Filed: Nov. 8, 2012

(86) PCT No.: PCT/US2012/064207
§ 371 (c)(1),
(2) Date: May 8, 2014

(87) PCT Pub. No.: WO2013/070954
PCT Pub. Date: May 16, 2013

(65) Prior Publication Data
US 2014/0298990 A1      Oct. 9, 2014

Related U.S. Application Data

(60) Provisional application No. 61/557,626, filed on Nov. 9, 2011.

(51) Int. Cl.
*G01N 30/46* (2006.01)
*G01N 30/60* (2006.01)
*G01N 30/72* (2006.01)

(52) U.S. Cl.
CPC .............. *G01N 30/461* (2013.01); *G01N 30/46* (2013.01); *G01N 30/463* (2013.01);
(Continued)

(58) Field of Classification Search
CPC ..... G01N 30/46; G01N 30/461; G01N 30/463; G01N 30/465; G01N 30/6095; G01N 30/466; G01N 30/468
USPC ............................................ 96/104
See application file for complete search history.

(56) References Cited

U.S. PATENT DOCUMENTS

| | | |
|---|---|---|
| 5,196,039 A | 3/1993 | Phillips et al. |
| 2003/0106363 A1 | 6/2003 | Sacks et al. |

(Continued)

FOREIGN PATENT DOCUMENTS

| | | |
|---|---|---|
| KR | 20030067220 A | 8/2003 |
| WO | WO-2005/024376 A2 | 3/2005 |

OTHER PUBLICATIONS

Hinshaw, John V., "Comprehensive Two-Dimensional Gas Chromatography," GC Connections, LCGC Europe, pp. 2-7 (Feb. 2004).

(Continued)

*Primary Examiner* — Robert Clemente
(74) *Attorney, Agent, or Firm* — Harness, Dickey & Pierce, PLC

(57) ABSTRACT

The present disclosure provides adaptive methods for gas chromatography analysis of a gas sample comprising one or more target analytes (such as a micro-gas chromatography) and adaptive gas chromatography devices for carrying out such analytical methods. Broadly, the system can regulate flow into a downstream chromatographic column by detecting one or more upstream conditions. For example, one adaptive chromatography device comprises a first column, a modulator component, and a second column. A first detector or sensor detects the presence of target analytes upstream from the second column, while a second detector detects the presence of target analytes eluted from the second column. The modulator component assembly is responsive to an output generated by the first detector and adaptively regulates fluid flow into the second column. Such adaptive chromatography (micro-GC) systems have higher separation speed, better analyte identification capability, and far greater energy savings.

19 Claims, 17 Drawing Sheets

(52) U.S. Cl.
CPC ........... *G01N 30/465* (2013.01); *G01N 30/466* (2013.01); *G01N 30/468* (2013.01); *G01N 30/6095* (2013.01); *G01N 30/72* (2013.01)

(56) References Cited

U.S. PATENT DOCUMENTS

| | | | |
|---|---|---|---|
| 2003/0118481 | A1 | 6/2003 | Briscoe et al. |
| 2009/0150087 | A1* | 6/2009 | Steinecker ............ G01N 30/461 702/24 |
| 2009/0178563 | A1 | 7/2009 | Masel et al. |
| 2009/0272270 | A1 | 11/2009 | McGill et al. |
| 2010/0101411 | A1 | 4/2010 | Tipler |
| 2011/0153225 | A1 | 6/2011 | Mangal et al. |
| 2013/0169970 | A1 | 7/2013 | Fan et al. |
| 2014/0017700 | A1 | 1/2014 | Fan et al. |

OTHER PUBLICATIONS

Hinshaw, John, "Gas Chromatography at the 26th International Symposium on Capillary Chromatography and Electophoresis," GC Connections, LCGC Europe, pp. 2-5 (Oct. 2003).

Liu, Jing, "Demonstration of a Two Dimensional Micro-Gas Chromatography System," Poster Session, 2012 Pittcon Conference & Expo, Session 850: GC Optimization (Mar. 12, 2012) (Abstract and p. 54 of Final Program).

Liu, Jing, et al., "Demonstration of motionless Knudsen pump based micro-gas chromatography featuring micro-fabricated columns and on-column detectors," Lab on a Chip, vol. 11, pp. 3487-3492 (Aug. 25, 2011) (downloaded on Jan. 9, 2012).

Liu, Jing, et al., "Fabry-Pérot Cavity Sensors for Multipoint On-Column Micro Gas Chromatography Detection," Anal. Chem., vol. 82, No. 11, pp. 4370-4375 (Jun. 1, 2010) (published online May 4, 2010).

Liu, Jing, et al., "Highly versatile fiber-based optical Fabry-Pérot gas sensor," Optics Express, vol. 17, No. 4, pp. 2731-2738 (Feb. 16, 2009) (published online Feb. 10, 2009).

Liu, Jing, et al., "Smart multi-channel two-dimensional micro-gas chromatography for rapid workplace hazardous volatile organic compounds measurement," Lab on a Chip, vol. 13, pp. 818-825, and Supplementary Information (7 pages) (2013).

Najafi, Khalil, "Micromachined Gas Chromatography Microsystem for Complex Gas Analysis," Presented at DARPA Microsystems Technology Symposium, San Jose, California (Mar. 7, 2007) (34 pages).

Reddy, Karthik, et al., "On-chip Fabry-Pérot interferometric sensors for micro-gas chromatography detection," Sensors and Actuators B: Chemical, vol. 159, pp. 60-65 (2011) (published online Jun. 15, 2011).

Reidy, Shaelah, et al., "A Microfabricated Comprehensive Two-Dimensional Gas Chromatography System," (Transducers) IEEE International Conference on Solid-State Sensors, Actuators, and Microsystems Workshop, Hilton Head Island, South Carolina, pp. 78-81 (Jun. 2010).

Shopova, Siyka I., et al., "On-Column Micro Gas Chromatography Detection with Capillary-Based Optical Ring Resonators," Anal. Chem., vol. 80, pp. 2232-2238 (2008) (published online Feb. 14, 2008).

International Search Report and Written Opinion for PCT/US2012/064207, mailed Mar. 18, 2013; ISA/KR.

* cited by examiner

-- Prior Art --

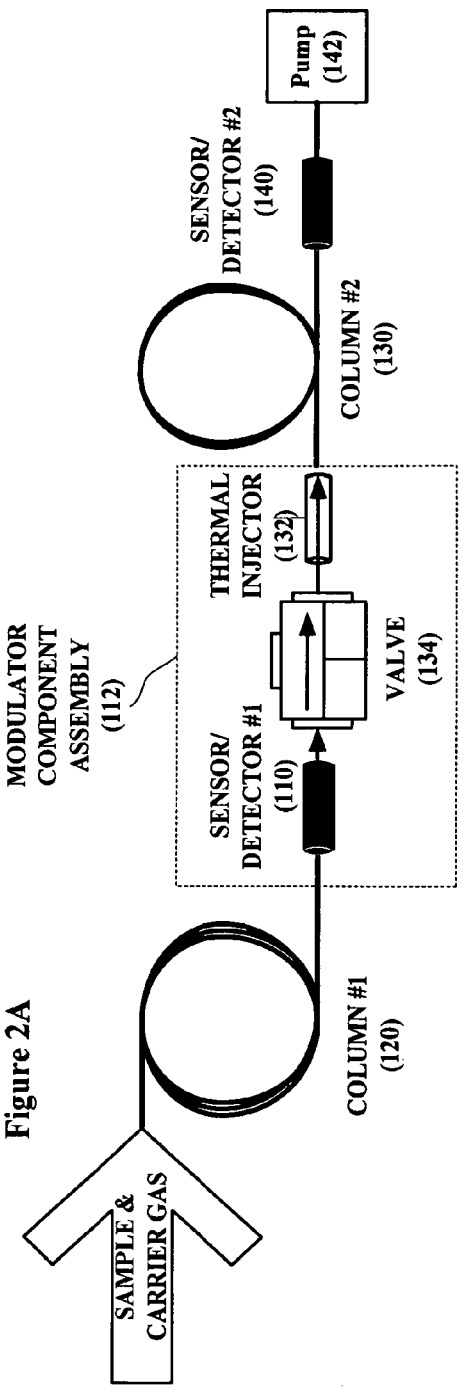
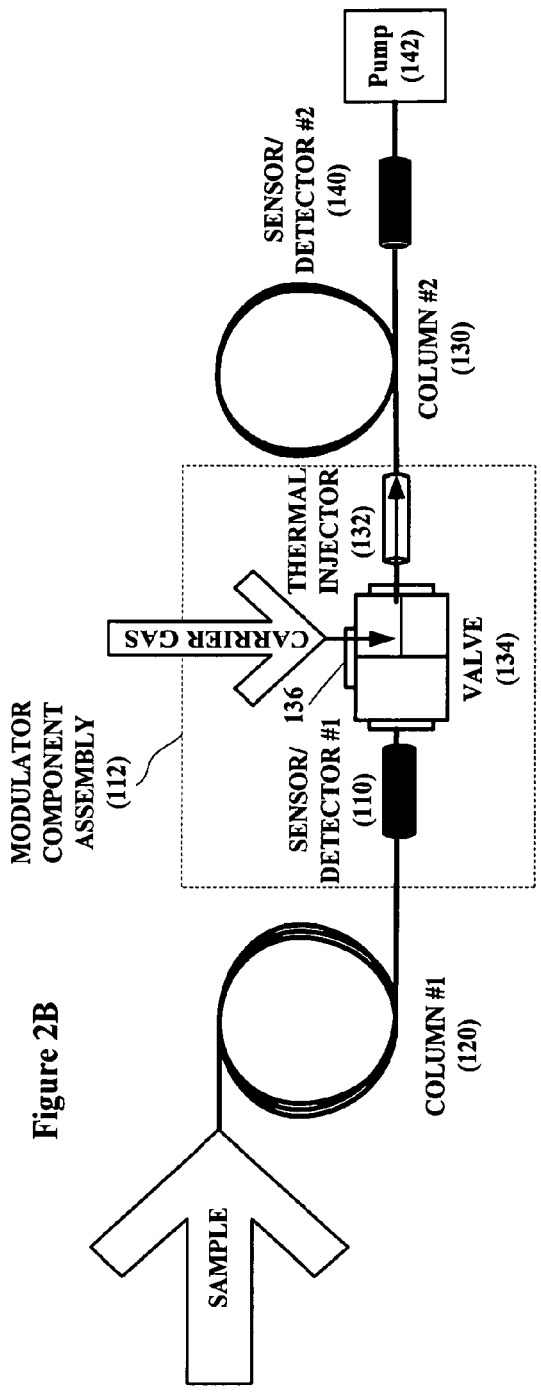

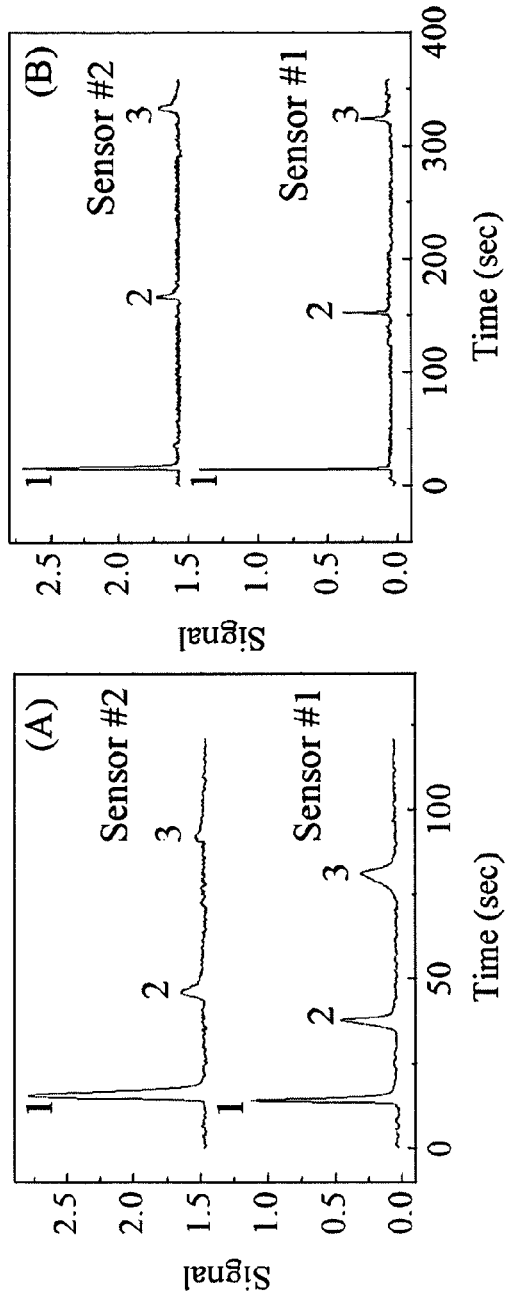
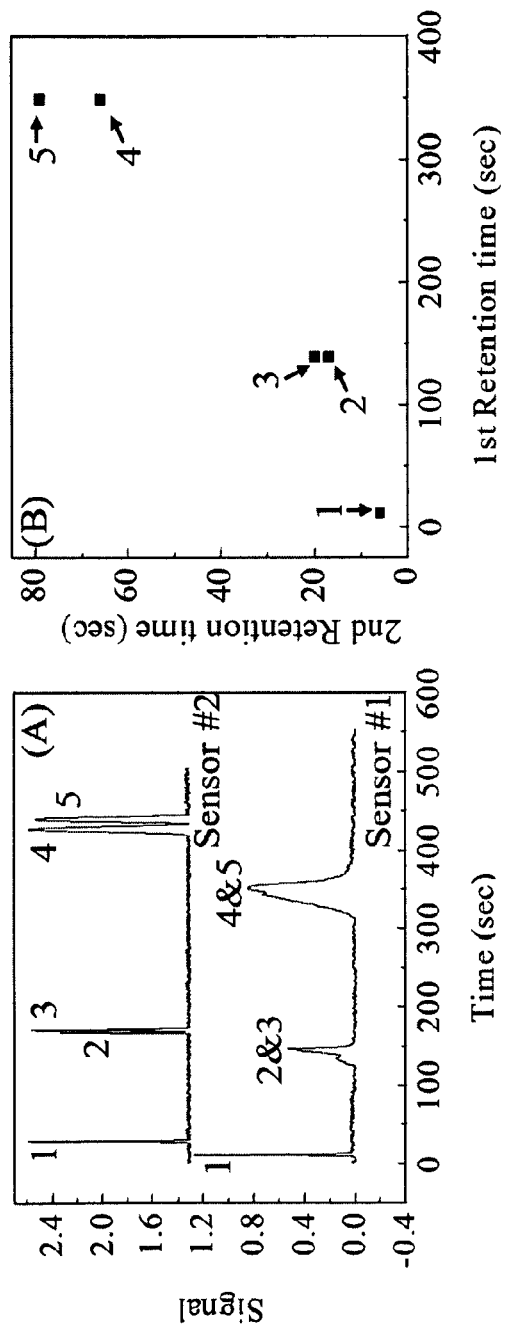
Figure 3
Figure 4

A: First GC Column
B: Adaptive Modulator Component Assembly System - Decision Making Console/Controller (containing detector(s), modulator(s), timing device(s), and routing fluidics (e.g., valves)
C: Additional Second GC Column(s)
D: Detector(s)
1-7: Distinct Target Analyte Species

DEVICES AND METHODS FOR ADAPTIVE MICRO-GAS CHROMATOGRAPHY

CROSS-REFERENCE TO RELATED APPLICATIONS

This application is a 371 U.S. National Phase of PCT/US2012/064207, filed on Nov. 8, 2012 and published in English as WO 2013/070954 on May 16, 2013. This application claims the benefit of U.S. Provisional Application No. 61/557,626, filed on Nov. 9, 2011. The entire disclosures of the above applications are incorporated herein by reference.

GOVERNMENT RIGHTS

This invention is made with government support under ECCS0729903 awarded by the National Science Foundation. The government has certain rights in the invention.

FIELD

The present disclosure relates to devices and methods for conducting gas chromatography and more specifically to methods of using adaptive micro-gas chromatography devices.

BACKGROUND

This section provides background information related to the present disclosure which is not necessarily prior art. Gas chromatography (GC) is a common chemical analysis tool used to separate and identify target analytes, such as volatile organic compounds or semi-volatile organic compounds. GC is particularly useful for analyzing complex samples having multiple target analytes that need to be individually detected. Thus, GC is employed for analysis in a variety of different fields, including organic chemistry research; the petrochemical industry; for pharmaceutical and medical research and development; in medical and health care industries, nutrition and cosmetics, including for food, drink, flavoring, and fragrances; environmental science; and forensic sciences, among others. GC devices typically have an injector, a column, and a detector. Different chemicals or target analytes are introduced into the column in a sample via the injector and then pass through the column at different rates (due to each chemical's physical and chemical interactions with the material contained in the column). As the target analytes are eluted from (exit) the column, the detector can differentiate the species eluted over time based on the rate at which the analytes pass through the column. Such analytes can be electronically identified and/or quantified during or after the detection.

Micro-gas chromatography is conducted on a miniaturized scale from traditional gas chromatography. One specific type of micro-gas chromatography is comprehensive two-dimensional (2-D) gas chromatography ("GC×GC"). Comprehensive two-dimensional gas chromatography (GC×GC) is well-suited to analysis and separation of complex mixtures of volatile and/or semi-volatile compounds. Typically in a GC×GC separation, the sample is introduced via injection into a first chromatographic column. The target analyte species elute from this first column and can be trapped or periodically sampled by a downstream modulator device. The modulator device is disposed between the first column and the second column, and serves to continuously trap, focus, and re-inject components eluted from the first column into the second column (as a continuous injector for the second column). Thus, after collecting the eluted species from the first column, typical modulators periodically inject the collected contents into a second column at a predetermined regular interval (e.g., usually at intervals ranging from 2 to 5 seconds). Such injected fractions can be separated in the second column and elute into a downstream detector, where they can be identified and/or measured.

Generally, GC×GC or comprehensive two-dimensional gas chromatography utilizes two columns of differing selectivities connected in series by the modulator device. GC×GC provides increased peak capacity, improved peak resolution, and increased compound detectability. However, while GC×GC analysis generally provides high selectivity for analytes, it can require large amounts of energy. For example, a thermal modulator device consumes significant power during operation in a GC×GC system due to its frequent on/off cycles. Thus, improved, energy efficient gas chromatography devices and methods having high analyte selectivity and reduced processing times are needed.

SUMMARY

This section provides a general summary of the disclosure and is not a comprehensive disclosure of its full scope or all of its features.

In certain aspects, the present disclosure provides an adaptive gas chromatography device. Such an adaptive chromatography device may comprise a first chromatographic column that receives a sample comprising one or more target analytes and a modulator component assembly disposed downstream of and in fluid communication with the first chromatographic column. The modulator component assembly comprises a first detector for detecting the presence of one or more target analytes eluted from the first chromatographic column and a thermal injector device. The adaptive chromatography device also comprises a second chromatographic column disposed downstream of and in fluid communication with the modulator component assembly. A second detector for detecting the presence of one or more target analytes eluted from the second chromatographic column is provided, where the modulator component assembly is responsive to an output generated by the first detector to regulate fluid flow into the second chromatographic column.

In other aspects, an adaptive micro-gas chromatography device comprises a first micro-gas chromatographic column. The first micro-gas chromatographic column receives a sample comprising one or more target analytes. The adaptive micro-gas chromatography device further comprises a modulator component assembly disposed downstream of and in fluid communication with the first micro-gas chromatographic column, which regulates fluid flow into a plurality of downstream micro-gas chromatographic columns in fluid communication therewith. The modulator component assembly comprises a first on-column detector for detecting the presence of one or more target analytes eluted from the first micro-gas chromatographic column and a thermal injector device. The device further comprises an additional detector for each respective downstream micro-gas chromatographic column so as to detect the presence of one or more target analytes eluted therefrom. The first on-column detector generates an output received by the modulator component assembly to regulate fluid flow into the respective downstream micro-gas chromatographic columns.

In yet other aspects, the present disclosure provides a method for conducting adaptive chromatography analysis that optionally comprises separating a sample in a first chromatographic column to generate one or more eluted target analytes. The one or more eluted target analytes are introduced into at least one downstream chromatographic column for a second separation of the one or more eluted target analytes. One or more system conditions are detected upstream of the at least one downstream chromatographic column for regulating flow into the at least one downstream chromatographic column.

In other aspects, a method of adaptive chromatography analysis is provided that comprises separating a sample in a first chromatographic column. An output signal is generated by detecting one or more target analytes during or after the separating of the sample in the first chromatographic column. Flow is adaptively regulated into at least one downstream chromatographic column based on the generated output signal to further separate the sample in the at least one downstream chromatographic column so as to analyze at least a portion of the one or more target analytes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a simplified exemplary schematic showing a conventional comprehensive two-dimensional micro-gas chromatography (GC×GC) device.

FIGS. 2A-2B show schematics of an exemplary embodiment of a two-dimensional (2-D) micro-gas chromatography device prepared in accordance with certain aspects of the present teachings. FIG. 2A shows a modulator component assembly comprising a first detector, a thermal injector device, and a flow regulating device (e.g., three-way valve). The modulator component assembly is disposed between a first chromatographic column and a downstream second chromatographic column. Analytes from the first column can pass through the valve and enter the thermal injector device (and/or second column). FIG. 2B shows a situation where the valve is directly open to carrier gas. The flow of analytes from the first column is thus stopped. The analyte in the thermal injector device is introduced and pushed through the second column.

FIGS. 3A-3B show chromatograms for three alkanes ((1) pentane; (2) octane; (3) nonane) obtained from a two-dimensional micro-gas chromatography device in accordance with certain aspects of the present teachings, which lacks a thermal injector device. FIG. 3A shows chromatograms corresponding to the configuration shown in FIG. 2A, except lacking the thermal injector device. FIG. 3B shows chromatograms where the valve in the devices of FIGS. 2 and 3 are disconnected twice. The first disconnection is from 20 sec to 140 sec, and the second from 180 sec to 300 sec.

FIGS. 4A-4B show two dimensional (2-D) separation results obtained from a two-dimensional micro-gas chromatography device prepared in accordance with certain aspects of the present teachings, including an adaptive modulator component assembly that includes a thermal injector device. FIG. 4A shows chromatograms from two on-column sensors. The analytes are (1) pentane; (2) decane; (3) cis-3-hexenyl acetate; (4) nonane; and (5) 1-hexanol. Coelution peaks of Analytes 2 and 3 and Analytes 4 and 5 are detected by Sensor 1, while they are separated and detected by Sensor 2.

FIG. 4B shows 2-D chromatogram with retention time at the first and second column as the x and y axis, respectively. The retention time for the second column starts when the thermal injector device is turned on.

Figure 7:
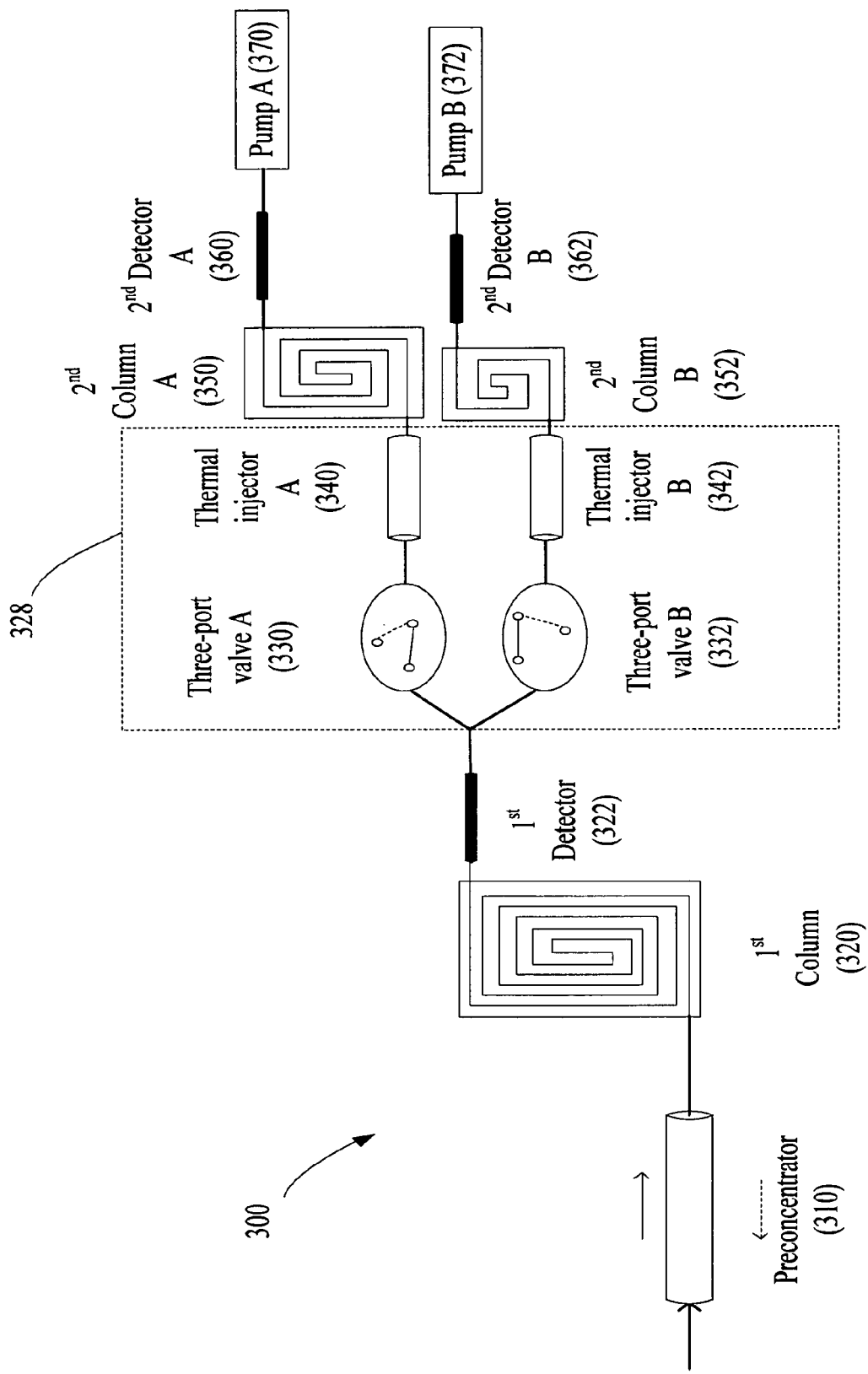
FIG. 7 shows an exemplary schematic of an alternative embodiment of an adaptive two-dimensional micro-gas chromatography (μGC) device that is automated and comprises GC×nGC columns (where n refers to the number of the second columns and is equal to 2).

FIGS. 8A-8D show images of a preconcentrator (8A), a micro-fabricated column formed by deep reactive ion etching a double spiral channel on a silicon substrate (8B), a micro-fabricated column having heaters and a thermocouple embedded (8C), respectively suitable for use in an adaptive multi-dimensional micro-gas chromatography (μGC) device like that in FIG. 7. 8D shows a schematic of operation of an on-column detector used in an adaptive multi-dimensional micro-gas chromatography (μGC) device like that of FIG. 7.

Figure 9:
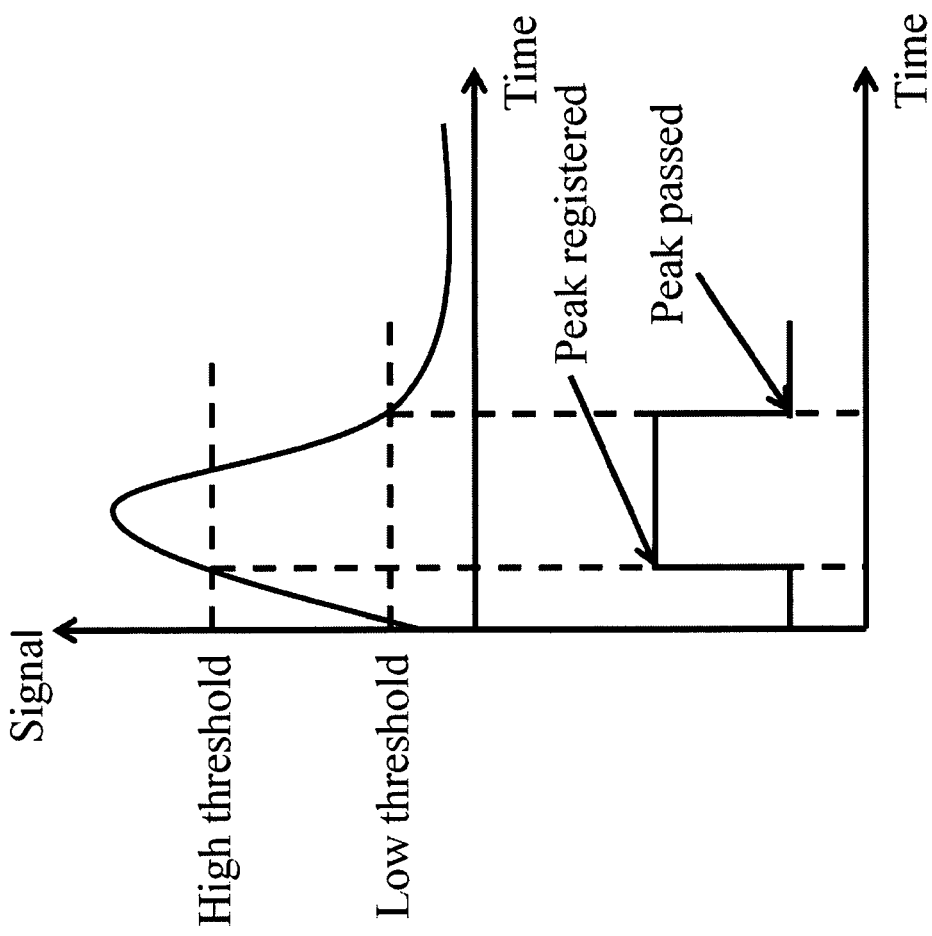

FIG. 9 is an illustration of a Schmidt trigger for use with a control/operation algorithm for use with an automated two-dimensional (2-D) micro-gas chromatography device according to certain aspects of the present disclosure.

Figure 10:
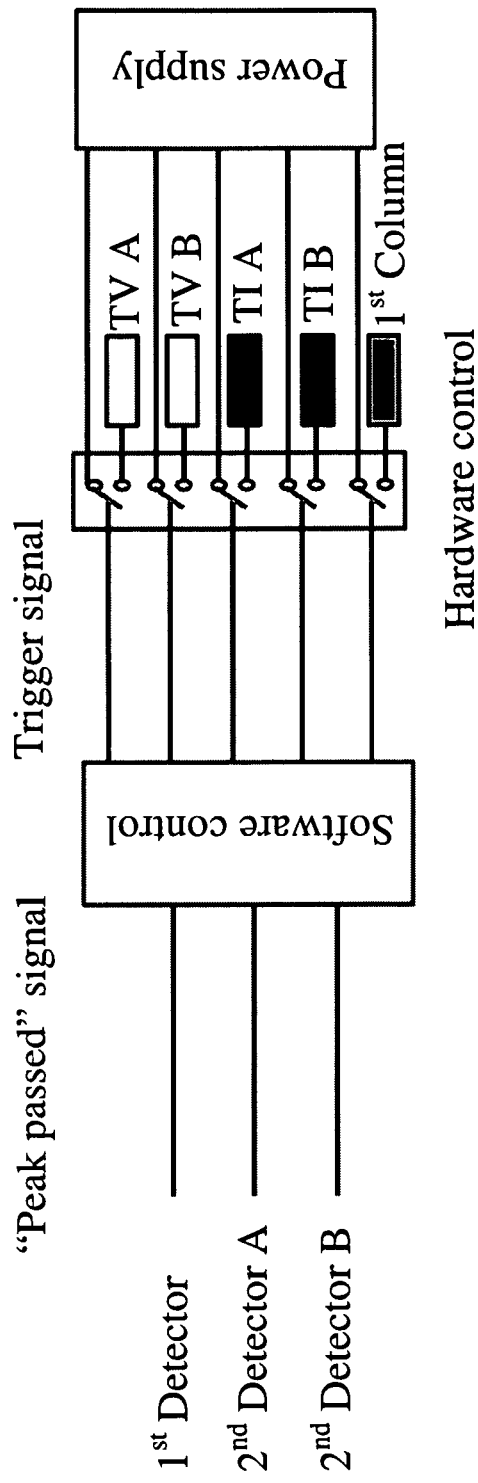

FIG. 10 is a schematic of a control/operation algorithm for use with an automated two-dimensional (2-D) micro-gas chromatography device according to certain aspects of the present disclosure. The TV is a three-port valve and TI is a thermal injector.

Figure 11A:
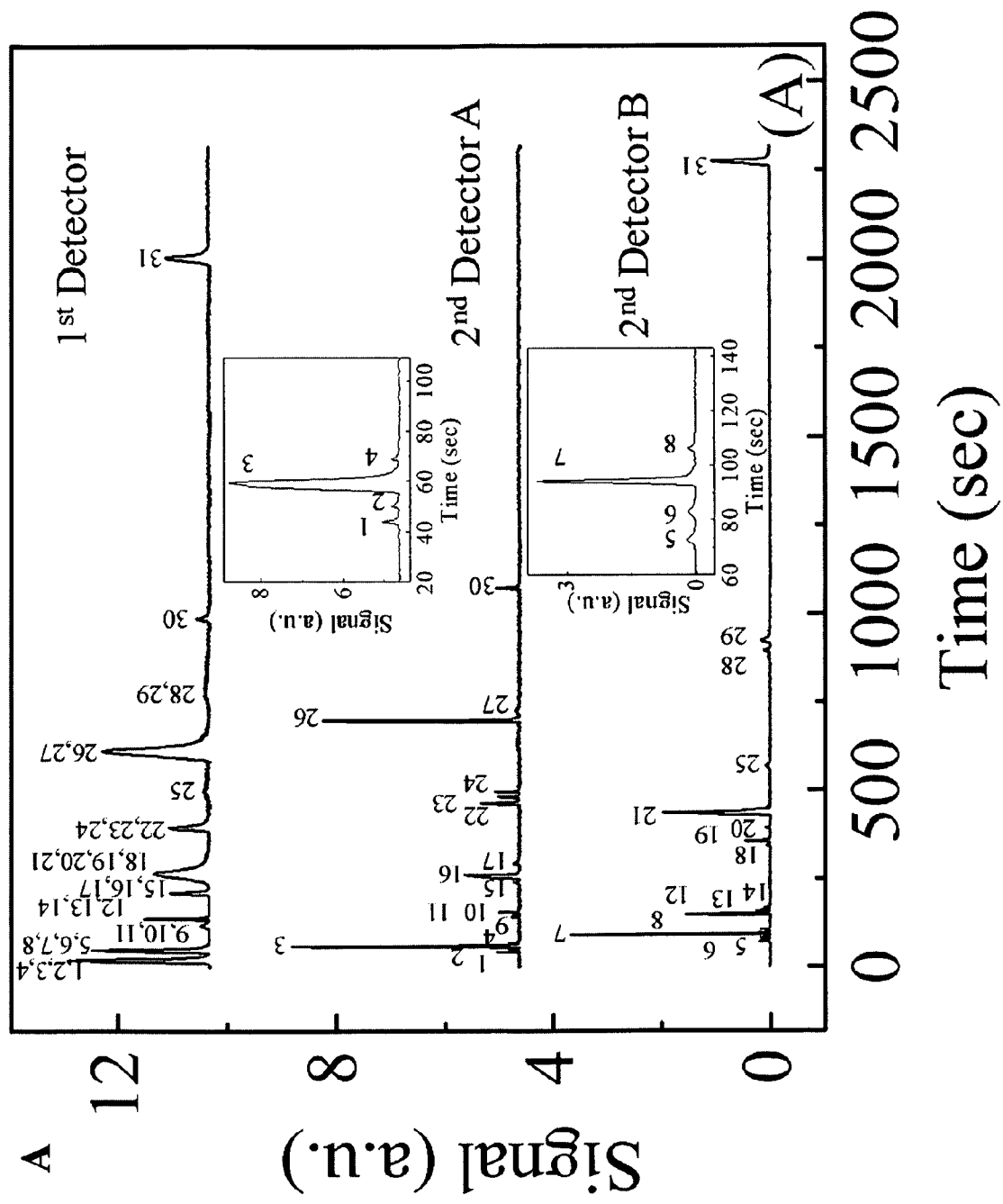
Figure 11B:
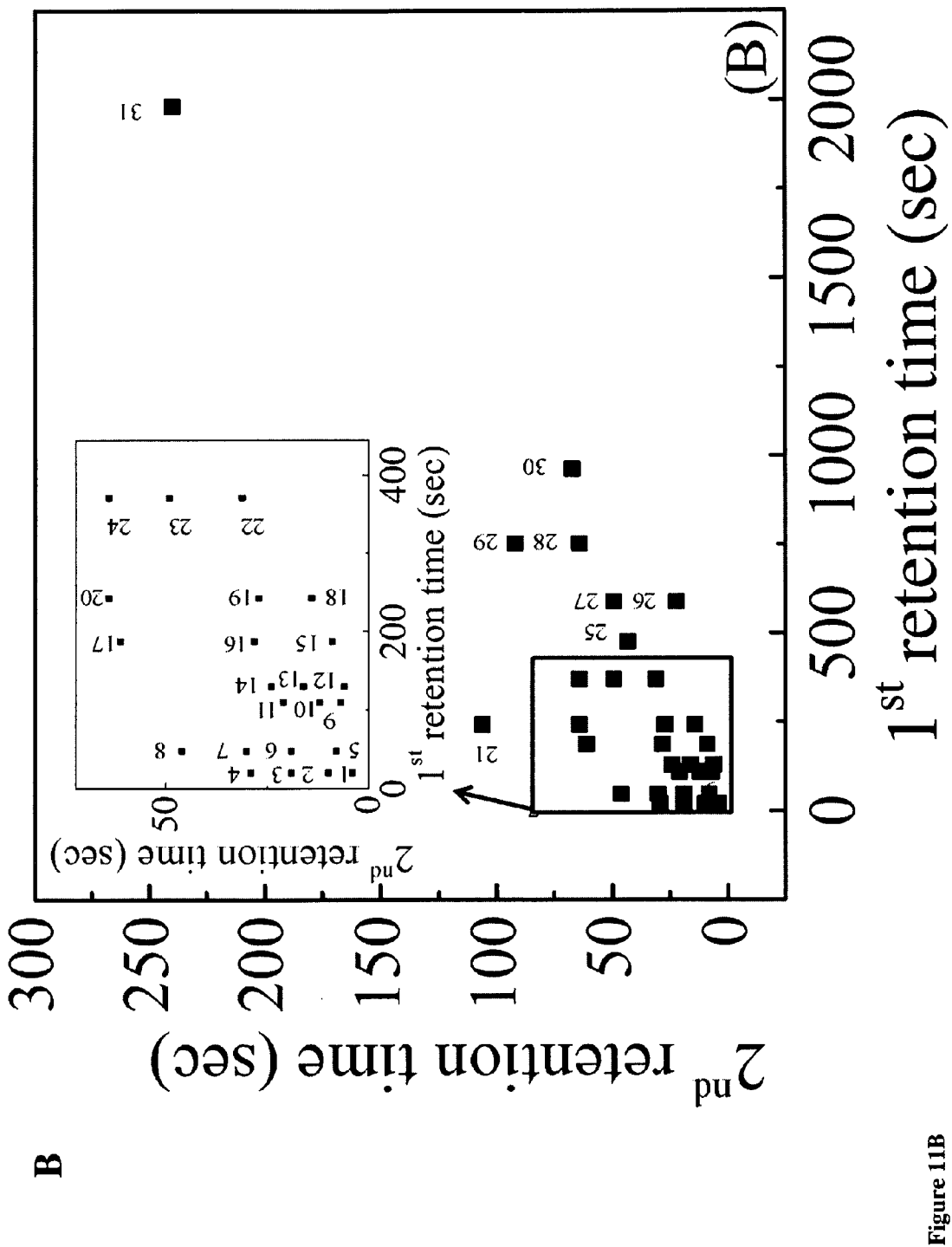

FIGS. 11A-11B show two dimensional (2-D) separation results obtained from an automated two-dimensional (2-D) micro-gas chromatography device prepared in accordance with certain aspects of the present teachings. FIG. 11A shows chromatograms from two on-column sensors. FIG. 11B shows 2-D chromatogram with retention time at the first and second column as the x and y axis, respectively. The retention time for the second column starts when the thermal injector device is turned on.

Figure 12:
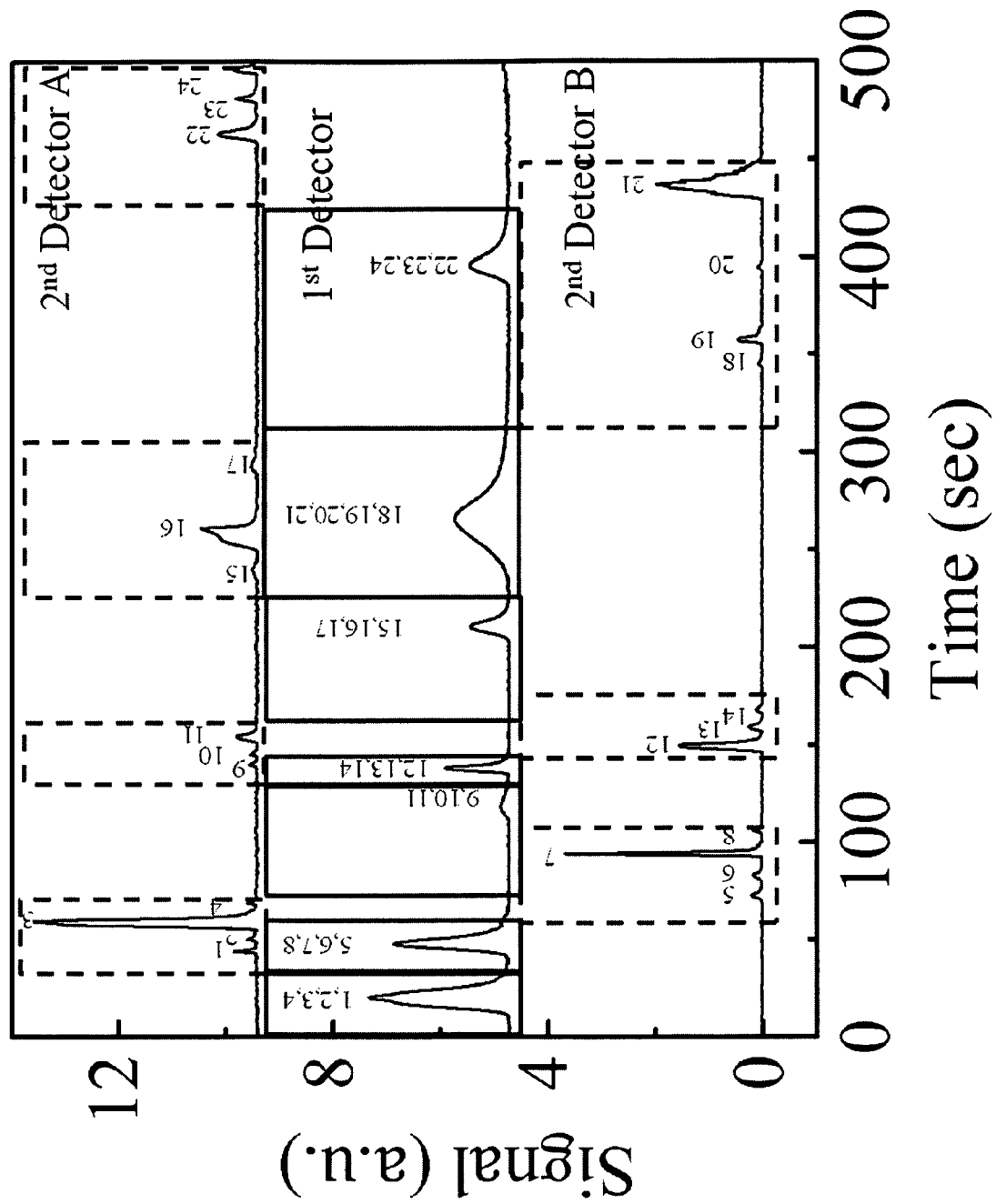

FIG. 12 is an enlarged part of FIG. 11A. Solid (dashed) boxes represent the separation duration at the first (second) column, while spaces outside the solid (dashed) boxes represent the duration when the separation at the first (second) column is suspended. Note that for better illustration, the entire real-time chromatograms for first detector and second detector A are vertically rearranged in comparison with original FIG. 11A.

Figure 13A:
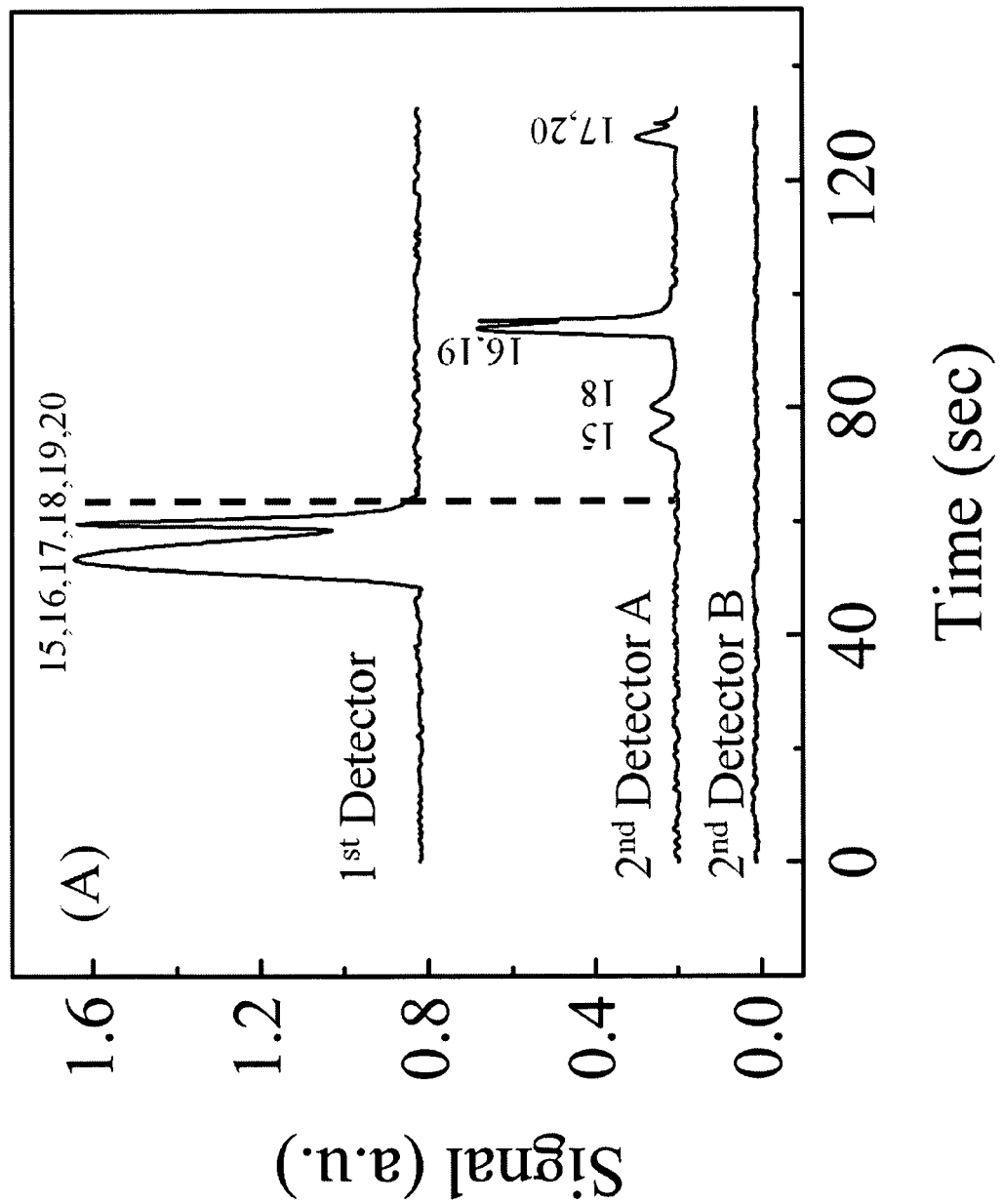
Figure 13B:
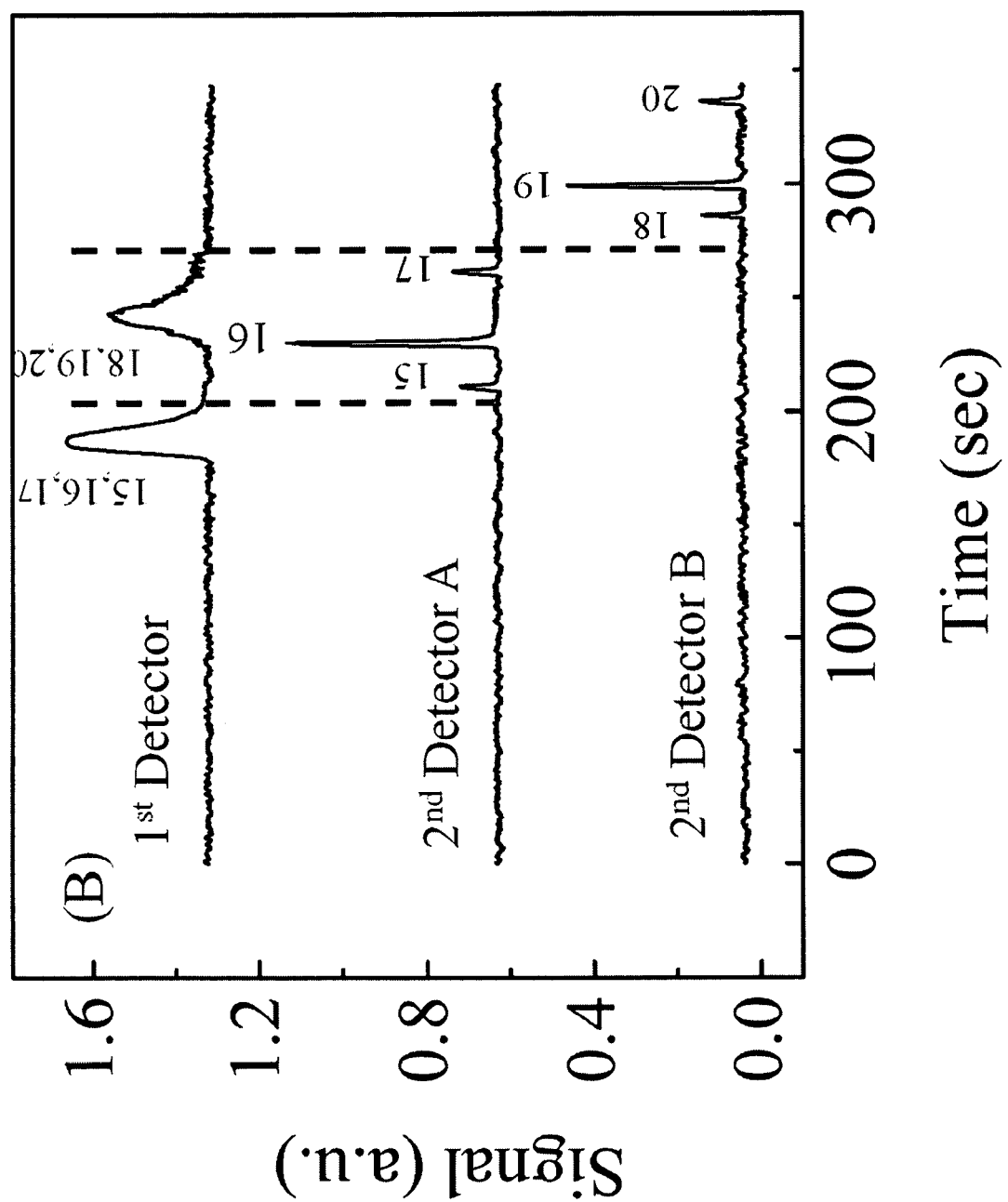

FIGS. 13A-13B show two dimensional (2-D) separation results obtained from an automated two-dimensional (2-D) micro-gas chromatography device prepared in accordance with certain aspects of the present teachings. FIGS. 13A and 13B show real-time chromatograms from three on-column sensors.

Figure 14A:
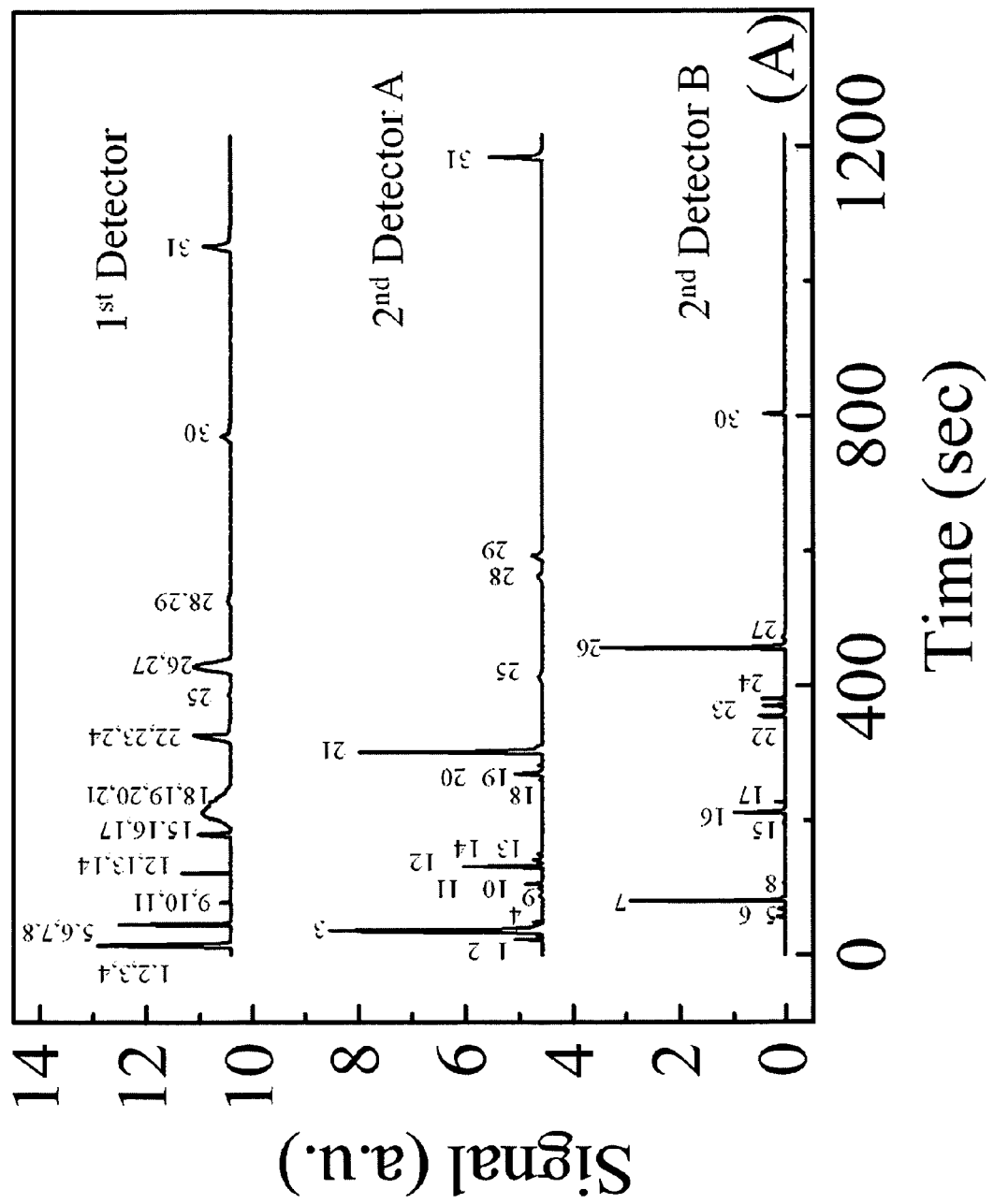
Figure 14B:
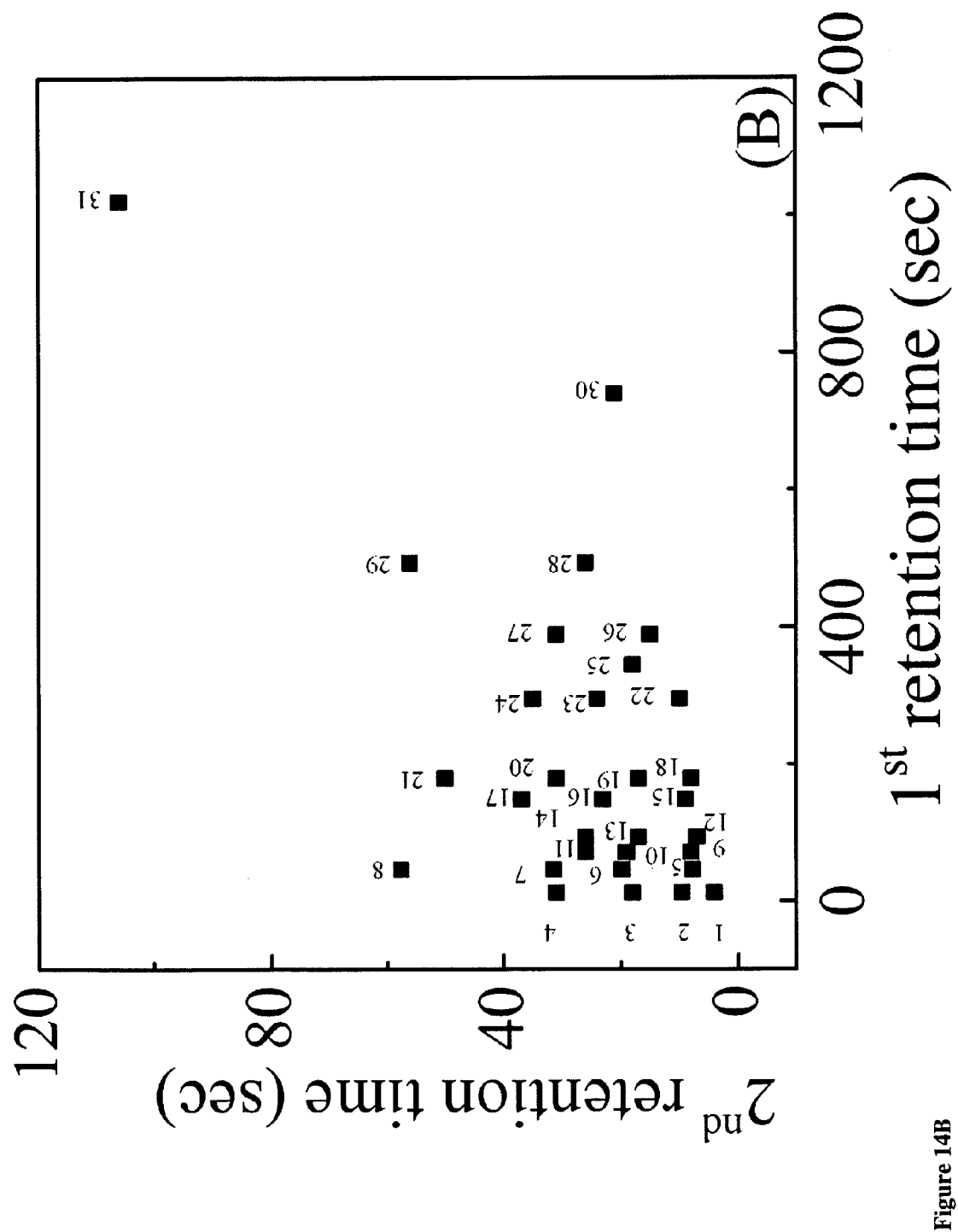

FIGS. 14A-14B show two dimensional (2-D) separation results obtained from another embodiment of an automated two-dimensional (2-D) micro-gas chromatography device prepared in accordance with certain aspects of the present teachings. FIG. 14A shows chromatograms from three on-column sensors. FIG. 14B shows 2-D chromatogram with retention time at the first and second column as the x and y axis, respectively. The retention time for the second column starts when the thermal injector device is turned on.

Figure 15:
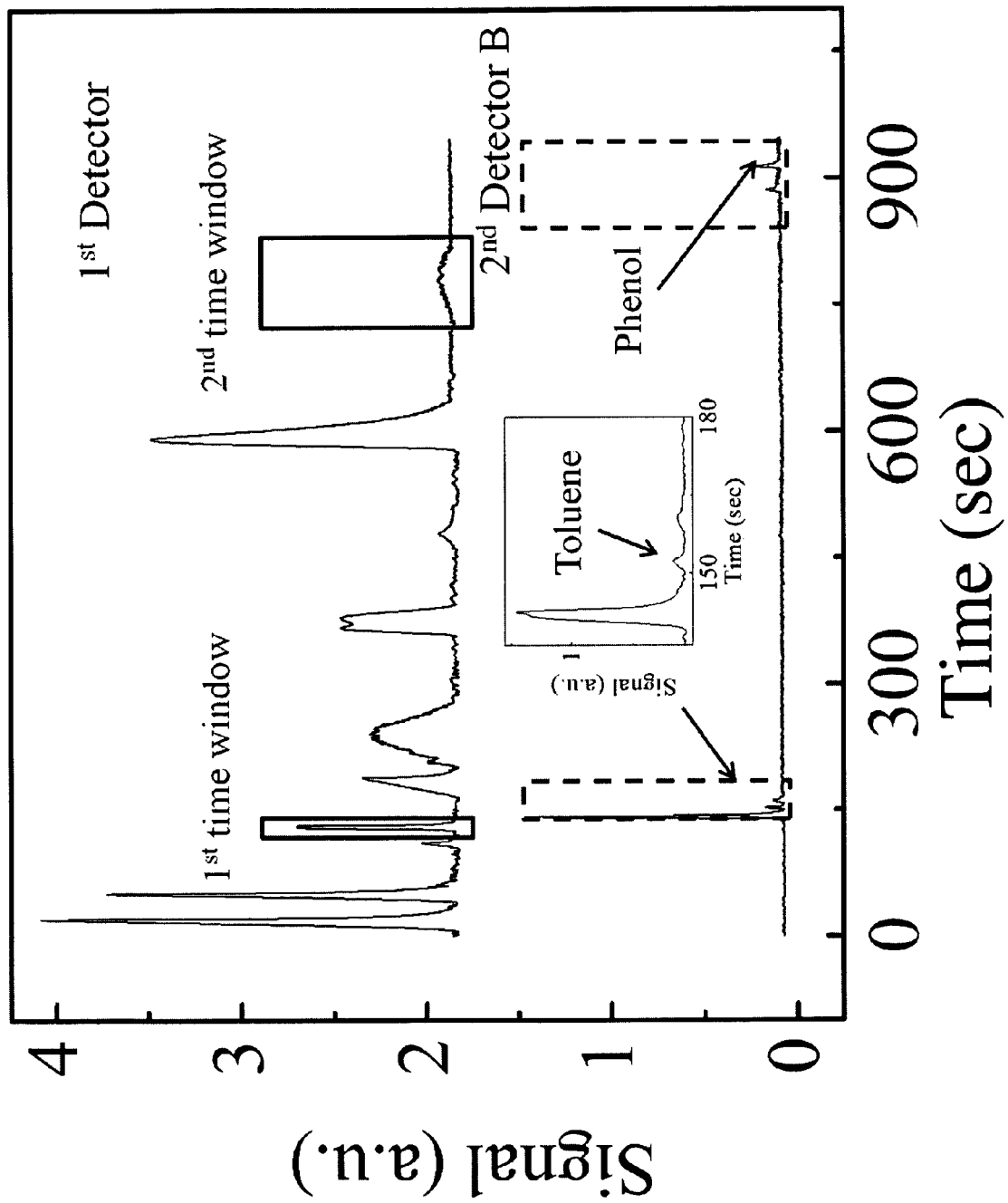

FIG. 15 shows two dimensional (2-D) separation results via a chromatograph obtained from yet another embodiment of an automated two-dimensional (2-D) micro-gas chromatography device prepared in accordance with certain aspects of the present teachings, where target analytes of interest are toluene and phenol.

Corresponding reference numerals indicate corresponding parts throughout the several views of the drawings.

DETAILED DESCRIPTION

Example embodiments are provided so that this disclosure will be thorough and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout this disclosure, the numerical values represent approximate measures or limits to ranges to encompass minor deviations from the given values and embodiments having about the value mentioned as well as those having exactly the value mentioned. Other than in the working examples provides at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges. Example embodiments will now be described more fully with reference to the accompanying drawings.

In various aspects, the present teachings pertain to gas chromatography analysis, more particularly to improved micro-gas chromatography devices and methods, such as two-dimensional micro-gas chromatography analytical devices that adapt to conditions. While certain concepts discussed herein that are related to adaptive chromatography are particularly well-suited to micro-gas chromatography techniques, the present teachings are not exclusively limited thereto, but rather, as can be appreciated by those of skill in the art, may be applicable to various other gas chromatography techniques. For a better understanding of the improved inventive features detailed herein, a conventional two-dimensional micro-gas chromatography device as depicted in FIG. 1 will be described herein.

Gas chromatography systems typically have five components: (1) a carrier gas supply; (2) a sample injection system; (3) one or more gas chromatography columns; (4) a detector; and (5) a data processing system. A carrier gas (also referred to as a mobile phase) is a high-purity and relatively inert gas, such as helium, hydrogen, nitrogen, argon, or air. The carrier gas in a conventional system flows through the column at the same time as the sample fluid to be tested (throughout the separating process). The sample injector introduces a predetermined volume of the sample mixture comprising one or more target analytes to be tested (e.g., in gaseous form) into the column by combining it with the flowing carrier gas from a carrier gas supply. Typically, separation is achieved within a chromatographic column because the inside surfaces of a column are coated (or the interior of the column is filled) with a material that serves as a stationary phase. The stationary phase adsorbs different target analytes in the sample mixture at differing degrees. The differences in adsorption cause differing delays and thus mobility rates for the different chemical species as they travel down the column, thereby effecting a physical separation of the target analytes in the sample mixture.

In a conventional system, a single detector is located at the end of one or more columns. The detector thus serves to detect the various chemicals or target analytes in the sample emerging or eluting from the column at different times. Such a detector typically operates in the gas chromatography system by destructive analysis of the eluted fractions. A data processing system is also typically in communication with the detector, so as to typically be able to store, process, and record the separation test results.

Figure 1:
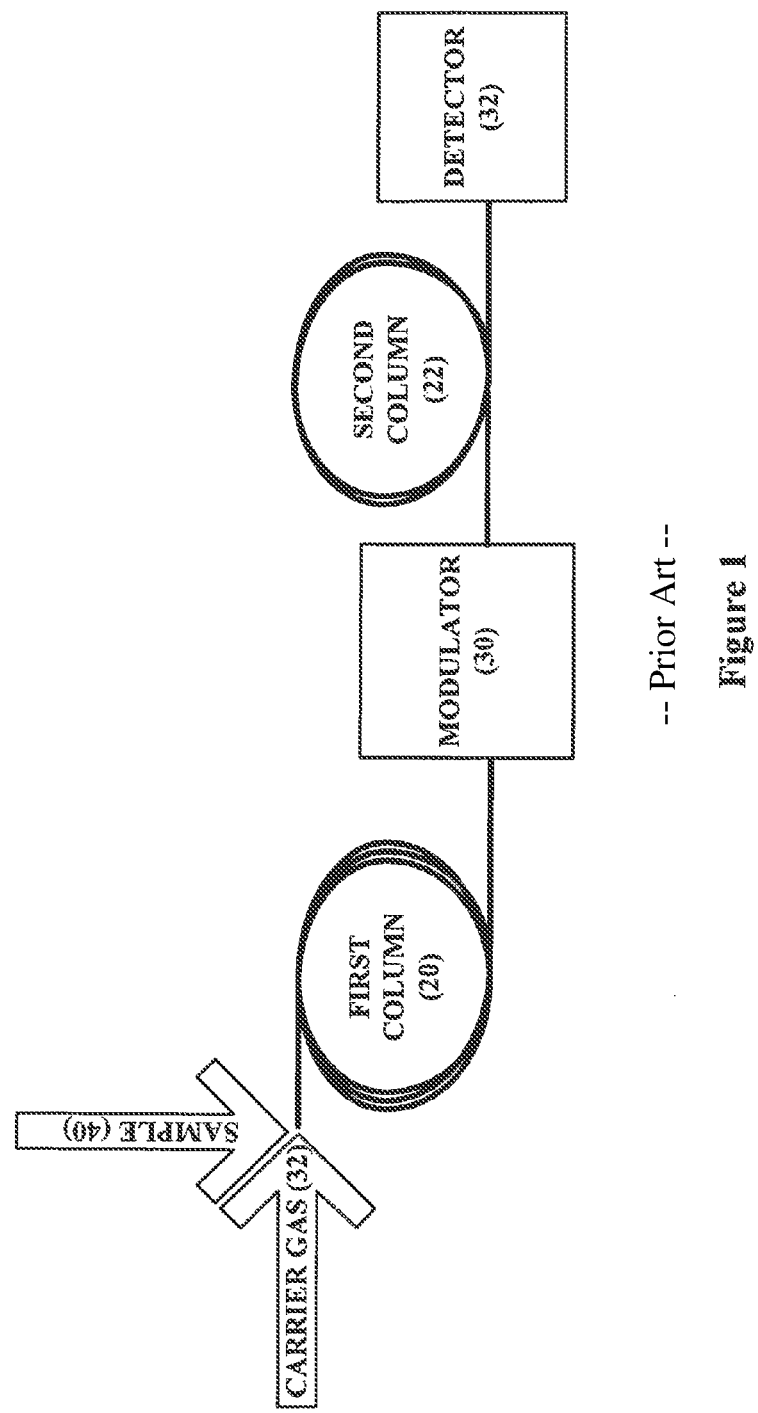

With reference to FIG. 1, a conventional GC×GC (comprehensive two-dimensional gas chromatography) apparatus 10 is shown that comprises two distinct chromatography columns (designated first column 20 and second column 22) fluidly connected in series with a modulation component (modulator 30) disposed therebetween. Each chromatographic column 20, 22 is selected to have different selectivities for the one or more target analytes, usually by containing distinct stationary phases in each respective column. For example, the first column 20 may be non-polar, while the second column 22 is polar or semi-polar or vice versa. Usually, the second column 22 is shorter than and has a diameter that is less than the first column 20. Such a second column can thus operate at high speed and separates one injected fraction prior to commencing separation of the next fraction at the next injected interval (e.g., several seconds later). The use of the term "column" is intended to broadly include various flow paths through which fluids may flow, such as a patterned flow field from micro-features defined in one or more substrates or other fluid flow paths recognized by those of skill in the art.

A carrier gas supply and a sample 40 (potentially having one or more target analytes) are introduced into the first chromatographic column 20. The sample 40 moves through with co-injected carrier gas from carrier gas supply. The target analyte species from the sample 40 is separated and transported through first column 20 and thus eluted therefrom. It is noted that the eluted sample having one or more target analytes may be eluted from the first column 20 in partial fractions, depending on the delay of the respective target analyte species as they are passed through and separated by the first chromatographic column 20. Further, the sample fractions that elute from the first column 20 may be optionally trapped and re-injected downstream. In a conventional gas chromatography system, the components eluted from the primary column 20 enter a detector for analysis. No modulator device 30 or secondary column 22 is present in such a conventional gas chromatography system.

However, in a two-dimensional gas chromatography system 10, a modulator device 30 and a secondary column 22 are disposed after and in fluid communication with the primary column 20. After exiting the primary column 20, the eluted samples 40 are processed by a modulator device 30 (instead of being directly analyzed by detector), so that the eluted sample is introduced to a secondary column 22 (having a distinct stationary phase from the primary column). Hence, a modulator device 30 is disposed between the first column 20 and the second column 22 and continuously collects and re-injects the components (the eluted sample) from the first chromatographic column 20 into the second chromatographic column 22.

One of the primary functions of a conventional modulator device 30 is to transform eluted peaks from the primary column 20 into a series of narrow pulses. Thermal modulation is the most common type of modulator device 30 and operates by concentrating samples as they emerge from the primary column 20 by collecting them in a retention region of the device. This retention is often done by rapid cooling of the gas stream for collection/retention, followed by rapid heating for desorption and release of the contents. The modulator device 30 thus serves as a continuous injector for the second column 22. In certain aspects, the modulator device 30 can sample effluent exiting the primary column 20 and transfers it via a pulse to the secondary column 22. The transferring process occurs at predetermined repeating modulation intervals or periods. The modulator 30 usually collects the eluent from the first chromatographic column 20 for a small fraction of the time, usually on the order of sub- to several seconds. Each fraction is re-focused into a very narrow band by the modulator device 30 and then sequentially injected into the second chromatographic column 22 for additional separation. Because the modulator device 30 makes the separation at two columns independently, analytes can be differentiated from each other by their respective retention times at the first and second chromatographic columns 20, 22, thus providing two dimensional separation information.

Thus, typical thermal modulator devices, such as that shown in FIG. 1, collect the eluted sample species from the first column 20 and periodically inject the collected contents into the second column 22 at predetermined intervals (e.g., usually at intervals ranging from sub-seconds up to 5 seconds). Such injected fractions are further separated in the second column 22 and eluted into a downstream detector 32 disposed after the second column 22. In typical operation, the sample fractions are quickly separated in the second column 22 and eluted into the detector 32, where they are identified and/or measured. The modulator device 30 typically controls the flow of analytes from the first column 20 to the second column 22, performing as a gate for injecting fractions in a consistent and reproducible fashion.

In spite of its enhanced separation capability, the conventional 2-D µGC suffers from several drawbacks, such as a high modulation frequency, which consumes a considerable amount of power and has high performance requirements for the modulator, and complicated re-construction of 2-D chromatogram, which requires extracting analytes' retention time at the first and second columns from limited and isolated information. The most significant limitation may be the short length of the second chromatographic column, as the second separation step must be completed within a modulation period (usually ranging from sub-second to a few seconds) in order to avoid the potential wrap-around issue. Consequently, the separation capability at the second column is severely degraded.

In a conventional system, a single detector like 32 can identify and optionally quantify the species eluted from the second chromatographic column 22, which is typically done by destructive analysis techniques. Typical detectors may be a mass spectrometer (MS) (e.g., a time-of-flight mass spectrometer (TOFMS)), a flame ionization detector (FID), an electron capture detector (ECD), or the like. The analytical detector device 32 in FIG. 1 is shown in a simplified version, so while not shown, such a system also has conventional heating elements, fluid flow regulators and conduits, and control electronics for sampling, heating, and acquisition of data, among other componentry. The analytical device can be associated with a data recording and processing unit (e.g., a computer or the like).

Multi-dimensional gas chromatography (GC×GC), such as that shown in FIG. 1, enables greater selectivity to improve the quality of separation of target analytes. However, as noted above, such conventional comprehensive two-dimensional gas chromatography analytical devices require excessive amounts of energy, due to frequent operation of the thermal modulating device (e.g., 30) at regular intervals. Thus, various aspects of the inventive technology improve such conventional gas chromatography analytical devices by reducing energy consumption, while improving analyte selectivity and detection and reducing processing times.

In various aspects, the present disclosure provides methods for adaptive chromatography, such as adaptive multi-dimensional gas chromatography. Such methods may include conducting adaptive chromatography analysis by first separating a sample in an upstream chromatographic column followed by introducing the sample (eluted from the upstream chromatographic column) into a distinct downstream chromatographic column, where a second separation process occurs. One or more conditions are detected in the system upstream of the downstream chromatographic column. Such conditions may include one or more selected from the group consisting of: target analyte chemical species, temperature, pressure, gas flow velocity and the like, and any combinations thereof. The one or more conditions may be measured at different points in the overall flow path before or upstream of the downstream chromatographic column. Detecting changes in one or more of these upstream conditions is then used to conditionally alter or modify one or more downstream conditions. Thus, in certain variations, one or more system conditions are detected upstream of the downstream chromatographic column and changes in one or more system conditions regulates flow into the downstream chromatographic column. For example, detecting one or more conditions in an upstream sensor associated with the first chromatographic column can generate an output signal that controls system components (e.g., modulator device and/or fluid regulators) so as to control and regulate flow of the eluted sample into the second downstream chromatographic column.

Thus, based upon such principles, the present disclosure also provides a novel adaptive micro-gas chromatography (micro-GC) system design. In various aspects, a plurality of detectors or sensors is used to adaptively regulate flow in the system and reduce energy consumption. For example, in certain aspects, one or more detectors can be used to non-destructively detect the gas or analyte flow inside a micro-fluidic channel corresponding to chromatographic columns, so that the gas flow can be routed or controlled (e.g., conditional flow routing or control) into downstream channels of chromatographic columns, depending on output signal(s) generated from those on-column detectors. The term "microfluidic channel" can include one or more fluid flow paths having dimensions of tens to hundreds of micrometers. As used herein, the term "fluid" is intended to broadly encompass gases, liquids, vapors, semi-liquids, and suspensions of solids in liquids or gases.

Thus, in certain variations, the present disclosure provides an adaptive chromatography device that comprises a first chromatographic column that receives a sample comprising one or more target analytes. Such a first chromatographic column may optionally comprise a micro-fluidic channel or column. An adaptive modulator component assembly is disposed downstream of and in fluid communication with the first chromatographic column. In various aspects, the modulator component assembly is an improved modulation system that provides the ability for adaptive response of the system in contrast to conventional modulator devices. The adaptive chromatography device also comprises at least one second chromatographic column disposed downstream of and in fluid communication with the modulator component assembly.

In certain variations, the modulator component assembly of the present disclosure optionally comprises a thermal injector device, optionally one or more flow regulators, like valves, and may further include one or more detectors. Thus, in certain aspects, the modulator component is an assembly of distinct components providing the ability to adaptively control flow in the system (e.g., "a decision console" or controller) by being responsive to one or more output signals in the system. For example, in accordance with certain aspects of the present teachings, the adaptive chromatography device comprises a modulator component assembly that comprises a first detector and a thermal injector device. The first detector in the modulator component assembly thus detects the presence of one or more target analytes either within or after being eluted from the first chromatographic column. The modulator component assembly, including the modified thermal injector device, is thus responsive to an output signal generated by the first detector and thus regulates fluid flow into the second chromatographic column (based upon detection of conditions in the first column) so as to provide the adaptive capabilities of the inventive chromatography device. It should be noted that in certain preferred aspects, the modulator component assembly comprises a plurality of associated components in close proximity in the system to one another (e.g., a first detector, flow regulators, and a thermal injector). However, the respective components of the modulator component assembly, while cooperating together so as to adaptively regulate flow to downstream columns, do not necessarily have to be physically close to one another in the system.

In certain aspects, the adaptive chromatography device further comprises a second detector to detect the presence of one or more target analytes eluted from the second chromatographic column. In certain variations, the output generated by the first detector is a first output and a second output is generated by the second detector. The modulator component assembly is responsive to both the first output and the second output and hence is capable of regulating fluid flow in both the first chromatographic column and the second chromatographic column. It should be noted that a plurality of downstream chromatographic columns may be employed after the first chromatographic column and the modulator component assembly. Thus, each of these downstream chromatographic columns may respectively have an additional detector, each of which may generate additional output signals that further regulate flow into these downstream chromatographic columns, as appreciated by those of skill in the art.

In yet other aspects, an adaptive chromatography device is provided that is a micro-gas chromatography device (μGC). Such an adaptive chromatography device comprises a first micro-gas chromatographic column. The first micro-gas chromatographic column optionally comprises a micro-fluidic channel. A modulator component assembly is disposed downstream of and in fluid communication with the first chromatographic column. The modulator component assembly comprises a first detector, such as an on-column detector associated with the first micro-gas chromatographic column, to detect the presence of one or more target analytes eluted from the first micro-gas chromatographic column. The first micro-gas chromatographic column receives a sample that potentially comprises one or more target analytes. Further, a second micro-gas chromatographic column comprising a second detector is provided. The second detector detects the presence of at least a portion of one or more target analytes eluted from the second micro-gas chromatographic column. The second micro-gas chromatographic column is disposed downstream of and in fluid communication with the modulator component assembly. The modulator component assembly is responsive to an output generated by the first detector to regulate fluid flow into the second micro-gas chromatographic column. As noted above, in certain variations, the modulator component assembly may also be responsive to additional output signals in the chromatography system and may regulate flow into the first micro-gas chromatographic column and the second micro-gas chromatographic column accordingly.

In various aspects, the present teachings provide (1) an ability to generate or detect conditions that initiate an adaptation process during operation of the chromatography device and (2) a nature of and the means to achieve such an adaptation process (such as flow routing and control). By incorporating such an adaptive concept into a micro-gas chromatography analytical device, for example, as part of the modified modulator component assembly, the system is more versatile and has simplified GC analysis processes than conventional systems. In various aspects, the adaptive micro-gas chromatography (micro-GC) system provides an analytical device with higher separation speed, better analyte identification capability, and higher savings in power consumption than in conventional micro-GC devices, like in FIG. 1.

In one embodiment of the present teachings, a plurality of on-column detectors is placed on or after each respective column. It is noted that by "on-column" it is meant that the detector is closely associated with the chromatographic column; for example, the detector may be disposed in, on, or near an exit of the chromatographic column, or alternatively disposed in near proximity to the chromatographic column, but downstream in a flow path through which the eluted sample fractions pass (see, e.g., Sensor 1 (110) in FIGS. 2A-2B). As noted above, a modulator component assembly may comprise the first detector associated with the first chromatographic column (see modulator component assembly 112 of which Sensor 1 (110) is a part in FIGS. 2A-2B). It is preferred that the first detector non-destructively analyzes the eluted sample from the first chromatographic column. In certain variations, such an on-column detector can be an on-column vapor detector. In certain variations, a detector may be an on-column optical detector.

In certain aspects, suitable detectors for selection as the first detector, like 110 in FIG. 2A, should preferably be non-destructive (e.g., consumes no analytes); compatible with micro-gas GC fluidics (e.g., does not introduce any dead volume and does not impart disturbance to the gas flow). In certain variations, a suitable non-destructive on-column optical detector comprises a capillary based optical ring resonator (CBORR) device. Such CBORR optical detectors for gas chromatography are described more fully in Shopova, Siyka I., et al., "On-Column Micro Gas Chromatography Detection with Capillary-Based Optical Ring Resonators," *Analytical Chemistry*, Vol. 80, No. 6, pp. 2232-2238 (Mar. 15, 2008) (published online Feb. 14, 2008), the contents of which are incorporated herein by reference in its entirety. Other detectors contemplated include Fabry-Pérot based interferometer vapors sensors, such as those described in Liu, Jing, et al., "Highly versatile fiber-based optical Fabry-Pérot gas sensor," *Optics Express*, Vol. 17, No. 4, pp. 2731-2738 (Feb. 16, 2009) (published online Feb. 10, 2009); Liu, Jing, et al., "Fabry-Pérot Cavity Sensors for Multipoint On-Column Micro Gas Chromatography Detection," *Analytical Chemistry*, Vol. 82, No. 11, pp. 4370-4375 (Jun. 1, 2010) (published online May 4, 2010); Liu, Jing, et al., "Demonstration of motionless Knudsen pump based micro-gas chromatography featuring micro-fabricated columns and on-column detectors," *Lab Chip*, Vol. 11, pp. 3487-3492 (2011) (published online Aug. 25, 2011); and Reddy, Karthik, et al., "On-chip Fabry-Pérot interferometric sensors for micro-gas chromatography detection," *Sensors and Actuators B: Chemical*, Vol. 159, pp. 60-65 (2011) (published online Jun. 15, 2011), each of which is expressly incorporated herein by reference in its entirety, chemi-resistor based vapor sensors, surface acoustic wave based vapor sensors, a thermal conductivity detector, or others known or to be discovered in the art.

In accordance with various aspects of the present teachings, a non-destructive detector forming part of the adaptive modulator component assembly is associated with and detects passage of eluted materials from a first chromatographic column. Furthermore, each chromatographic column present in the gas chromatography analytical device comprises at least one detector disposed thereon or disposed after the column to monitor the contents of the respective columns. Thus, a first on-column vapor detector can form part of the modulator component assembly and non-destructively detects one or more analytes passing through/eluted from the first GC column. A second GC separation column similarly has a second detector disposed near its exit to detect one or more target analytes eluting therefrom. The first detector or sensor may be of the same type as the second terminal detector or sensor or, alternatively, the first detector may be of a different type than the second sensor/detector. In other variations, where a plurality of additional chromatographic columns is employed downstream from the first chromatographic column and the modulator component, each respective chromatographic column comprises a detector for detecting the eluted species therefrom.

In various aspects, a modulator component assembly comprises a thermal injector device and a first sensor for detecting one or more target analytes exiting from the first chromatographic column. The thermal injector device is used to trap and re-focus the analytes from the first column and re-inject them into the second column for further separation; however, its operation deviates from traditional thermal injector device usage. The first on-column detector (as well as the second detector) provides important timing information (e.g., generation or detection of the "adaptation conditions") for the thermal injector device to activate or deactivate (e.g., turn on/off for conditional flow routing/control). In this manner, the thermal injector device is primarily in a stand-by or low-power consumption mode until it is triggered or activated by a signal generated from the first detector. As compared to the conventional 2-D micro-GC (or regular 2-D GC) design, where most power consumption occurs at the thermal injector/modulator device by rapid activation and deactivation throughout all operating periods, in the adaptive micro-GC design according to certain aspects of the inventive technology, power consumption is significantly reduced, because the thermal injector is only used intermittently.

Furthermore, in certain variations, the first on-column detector associated with the modulator component assembly can be placed at the end of the first column to provide chromatograms complementary to those obtained at the end of the second column, which simplifies the GC analysis process and enhances the analyte identification capability. As noted above, in certain variations, the first detector is non-destructive and compatible with micro-gas GC fluidics. The first detector may be the same as the second terminal sensor or may be different. Notably, in conventional 2-D micro-GC or regular 2-D GC designs, only a single solitary detector is employed at the terminal end of the second column for detection and analysis of eluted fractions.

One embodiment of the inventive adaptive micro-gas chromatography (μGC) analytical device is a two dimensional (2-D) μGC that comprises two distinct gas chromatographic columns. For example, such an adaptive micro-gas chromatography (μGC) analytical device integrates two GC columns with different selectivities (e.g., each column has a distinct coating), while also having two on-column optical detectors. One of the on-column detectors is included in the adaptive modulator component assembly and provides the ability to adaptively regulate flow in the system. The adaptive modulator component assembly also comprises a thermal injector device and may have a flow regulating device, such as a multi-port valve. The analytical device may further comprise one or more pumps.

One such embodiment of an inventive adaptive micro-gas chromatography (μGC) analytical device 100 is shown in FIGS. 2A-2B. A first chromatographic column 120 and a distinct second chromatographic column 130 are disposed in series and in fluid communication with one another. A modulator component assembly 112 comprises a first detector 110 (Sensor 1), a thermal injector device 132, and a flow regulating device in the form of a three-way valve 134. The first detector 110 detects the presence of one or more target analytes eluted from the first column 120 and provides a corresponding output signal in the modulator component assembly 112. The three-way valve 134 is disposed between the first column 120 and second column 130 and functions to regulate/switch the fluid connection between the first and second columns 120, 130. A second detector 140 (Sensor 2) is disposed after the second column 130. A pump 142 is placed at the end of the second column 130 to provide fluidic flow to the entire system.

The two on-column detectors (Sensors 1 and 2 (110, 140)) are included in the system to monitor and/or record retention time of each analyte from the corresponding column. As noted above, the first detector 110 is installed downstream of the first column 120 and forms part of the modulator component assembly 112, while the second detector 140 is installed downstream of the second column 130. In certain variations, such an on-column detector can be an on-column vapor detector, as discussed above. In certain variations, a detector may be an on-column optical detector. In certain variations, a suitable on-column optical detector for the first detector is non-destructive and comprises a capillary based optical ring resonator (CBORR) device, a Fabry-Pérot detector, a chemi-resistor sensor, a sound acoustic wave sensor, or a thermal conductivity detector, as discussed previously above. While the first and second detectors 110, 140 may be the same type of detector placed at different positions in the system, in other alternative variations, the first and second detectors may be different from one another. In addition to the detectors described above, a second detector may be an MS, FID, TOFMS, ECD, a thermal conductivity detector, or other detectors known or to be discovered in the art may also be employed.

The modulator component assembly 112 comprises a thermal injector device 132, which is disposed between the three-way valve 134 and the second column 130 (downstream of the first column 120 and first detector 110 (Sensor 1)). The thermal injector device 132 traps and collects the eluted fractions from the first chromatographic column 120. The thermal injector device 132 thus re-focuses the peak eluted out from the first column 120 (collected fraction(s)) and re-injects the eluted sample into the second column 130 by raising its temperature to a sufficient level. In accordance with certain principles described herein, the thermal injector device 132 is operated in an adaptive manner that saves energy and improves analytical capability of the chromatography device 100.

Generally, a gas chromatography method comprises three sequential steps in a 2-D μGC process. The first step in the process is separation in a first chromatographic column, followed by modulation, and finally separation in a second chromatographic column. In certain variations of the present teachings, a method for conducting adaptive chromatography analysis is provided that comprises the following. First, a sample is separated in a first chromatographic column. After elution from the first chromatographic column, an output is generated by detecting one or more target analytes during or after the separating of the sample in the first chromatographic column. The, flow into at least one downstream chromatographic column is adaptively regulated based on the generated output to further separate the sample in the at least one downstream chromatographic column, so as to analyze at least a portion of the one or more target analytes.

For example, in certain aspects, after elution from the first chromatographic column, the sample is introduced to an adaptive modulation component assembly. One or more target analytes are detected in the sample after elution from the first chromatographic column by the modulation component assembly. The modulation component detects the presence of one or more analytes by way of a first detector, where an output signal is generated based on the presence of the one or more target analytes. Such detecting and generating of an output signal may include continuous monitoring, where the level of the output signal varies from a baseline level to a peak level when one or more target analytes are detected.

The modulator component assembly further regulates flow of the sample into a second downstream chromatographic column. In various aspects, the present devices and methods provide an ability to control when vapor is routed between columns and when flow is shut off. Thus, the modulator component assembly adaptively regulates flow of the sample into the second micro-gas chromatographic column based on the output signal generated during the detecting of one or more analytes after elution from the first chromatographic column. In the second chromatographic column, the sample is further separated. A subsequent detecting step occurs for one or more target analytes eluted from the second chromatographic column.

In certain aspects, during the detecting, a baseline output signal is generated in the absence of the one or more target analytes (eluted from the first chromatographic column) and a peak output signal is generated in the presence of the one or more target analytes. In certain aspects, after the output signal reaches the peak output signal and subsequently falls to the baseline output signal, a modulator component assembly can be used to inhibit the flow of the sample from the first chromatographic column into the second chromatographic column for a predetermined period to permit the sample to pass through the second chromatographic column. Thus, flow through the first chromatographic column is inhibited or prevented during this predetermined period. The predetermined period depends upon the capacity of the system, the analytes to be detected, the volume and characteristics of the second chromatographic column, and the like. The duration of the predetermined period can widely range and in certain variations can be less than one second up to multiple hours. In certain variations, the predetermined duration may optionally be greater than or equal to about 300 seconds (5 minutes), optionally greater than or equal to about 330 seconds (5.5 minutes), optionally greater than or equal to about 360 seconds (6 minutes), optionally greater than or equal to about 390 seconds (6.5 minutes), optionally greater than or equal to about 420 seconds (7 minutes), and in certain variations, greater than or equal to about 600 seconds (10 minutes). The modulator device can trap and re-focus the eluted sample from the first chromatographic column, so that when the output signal falls from the peak output signal to the baseline output signal, the trapped eluted sample is rapidly heated in the modulator device and injected into the second chromatographic column.

After the sample passes through and is eluted from the second chromatographic column, one or more target analytes is further detected from the second chromatographic column (e.g., in a second detector). After the separating and eluting of the sample is completed (completion may be discerned based on the detecting of one or more analytes from the second column), flow through the first chromatographic column is then restored. In certain variations, a carrier gas is supplied to the modulator component assembly to flow with the sample introduced into the second chromatographic column during the predetermined period.

In other aspects, the modulator component assembly comprises a flow routing system, which may include flow regulating devices like three-way valves. In a first position, the flow regulating device, e.g., three-way valve, permits the sample to flow from the first chromatographic column into the second chromatographic column. In a second position, the flow regulating device, e.g., three-way valve, prevents the sample from flowing from the first chromatographic column into the second chromatographic column, but permits the carrier gas to enter the second chromatographic column. The output signal (generated during detecting of one or more analytes in the first column) is capable of changing the valve from the first position to the second position, for example, by controlling an actuator or other controller connected to the flow regulating device, e.g., valve mechanism.

In accordance with certain embodiments of the present teachings, the process may be conducted as follows. During the first step shown in FIG. 2A, the first chromatographic column 120 is in fluid communication with and connected to the second chromatographic column 130. A modulator component assembly 112 comprises a first detector 110, a thermal injector device 132 and at least one valve 134. The sample mixture is drawn into the system by the pump 142 placed at the end of the second column 130. The sample mixture is thus separated within and then eluted from the first column 120. At the second step, the first detector 110 (Sensor 1) associated with the modulator component assembly 112 detects a peak (a single analyte or a mixture of multiple analytes) eluted out from the first column 120. The eluted fluid from the first column 120 is then trapped and re-focused by the downstream thermal injector device 132 in the modulator component assembly 112 system. When the signal from first detector 110 (Sensor 1) returns to a baseline level (which means that the peak has passed through), the three-port valve 134 in the modulator component assembly 112 disconnects the first column 120 from the second column 140. A carrier gas can be drawn into the three-way or three-port valve 134 via a third port 136 as shown in FIG. 2B. Consequently, the flow rate in the second column 130 remains the same or even higher, while the flow at the first column 120 is completely stopped, suspending the flow of the analytes altogether. Meanwhile, the temperature of the thermal injector device 134 is ramped rapidly to re-inject the adsorbed/trapped analyte(s) into the second column 130. In the third step, the analyte(s) are further separated at the second column 130 and detected by the second detector 140 (Sensor 2). When no peak is detected by the second detector 140 within a pre-defined duration, the three-port valve 134 in the modulator component assembly 112 is switched back to the configuration shown in FIG. 2A to start the next three-step cycle until all of the analytes are detected.

Such an adaptive two-dimensional micro-gas chromatography (μGC) prepared in accordance with certain aspects of the present disclosure is demonstrated by the preliminary separation result of three distinct alkanes. FIGS. 3A-B show chromatograms of three alkanes obtained from an adaptive two-dimensional micro-gas chromatography (μGC) system in accordance with certain aspects of the present teachings, such as shown in FIGS. 2A-B; however, the adaptive modulator component assembly lacks a thermal injector device between the first and second columns. The first column is 1.5 m long and coated with RTX-1. The second column is 0.8 m long and coated with CARBOWAX™.

FIG. 3A shows the chromatograms obtained at the first detector (Sensor 1) and the second detector (Sensor 2) when the valve is adjusted to connect the first and second columns together (as shown in FIG. 2A). The analytes are (1) pentane; (2) octane; and (3) nonane. The retention time of the three alkanes at the first detector is 35 sec, 552 sec, and 1,381 sec, respectively. Flow through the valve is discontinued by adjusting the three-way valve to prevent flow from the first column into the second column. The disconnection occurs two different times to cease flow of analytes from the first column. The first disconnection is from 20 sec to 140 sec, and the second from 180 sec to 300 sec.

FIG. 3B shows the chromatograms obtained at two detectors when stop-flow is performed (where the three-way valve in the modulator component assembly blocks flow from the first column into the second column as in FIG. 2B). The valve is disconnected between the first and second columns two different times, first at 240 sec (for a duration of 360 sec) and again at 1,200 sec (again for a duration of 360 sec). As a result, the retention time of Analytes 2 and 3 is delayed for 355 sec and 700 sec, respectively. The delay of the retention time matches the disconnection time of the valve, which demonstrates that the flow at the first column is completely stopped and all analytes are suspended when flow through the valve in the modulator component assembly into the second column is discontinued.

The 2-D separation result is illustrated in FIGS. 4A-4B, where three analytes with different volatilities and polarities are successfully separated in one embodiment of the inventive adaptive micro-gas chromatography (μGC) analytical device according to the present teachings. Although Analytes 2 and 3 and Analytes 4 and 5 are coeluted at the first column, they are able to be separated at the second column by using the adaptive techniques described above.

FIGS. 4A-4B show 2-D separation results obtained from another embodiment of the adaptive two-dimensional micro-gas chromatography (μGC) similar to that shown in FIGS. 2A-2B, where a thermal injector device in the modulator component assembly is disposed between the first column and the second column. The first column is 1.5 m long and coated with RTX-1. The second column is 0.8 m long and coated with CARBOWAX™. The analytes are as follows: (1) pentane; (2) decane; (3) cis-3-hexenyl acetate; (4) nonane; and (5) 1-hexanol. FIG. 4A shows chromatograms from two on-column sensors. A first on-column detector (Sensor 1) is associated with the modulator component assembly, while a second on-column detector (Sensor 2) is associated with the second column. Coelution peaks of Analytes 2 and 3 and Analytes 4 and 5 are detected by Sensor 1. However, as can be seen in FIG. 3B, Analytes 2 and 3 and Analytes 4 and 5 are separated from one another and detected as separate peaks by Sensor 2. FIG. 4B is a 2-D chromatogram with retention time at the first column and second column as the x and y axis, respectively. The retention time for the second column starts when the thermal injector device is turned on. Again, FIG. 4B demonstrates separation of Analytes 2-3 and 4-5 from one another and detected as separate peaks by Sensor 2 when employing the adaptive techniques of the present technology.

It should be noted that the principles of the present disclosure pertaining to adaptive gas chromatography separation are not limited to a two-dimensional micro-gas chromatography (μGC). Rather, a plurality of columns may be employed serially and/or in parallel to one another. In one illustrative embodiment shown in FIG. 5, a modified 2-D GC design is shown. Instead of using one GC column followed in series by another GC column (conventional 2-D GC, also called GC×GC), the present teachings can include gas chromatography analytical devices having GC×nGC columns (where n refers to the number of the second columns), nGC×GC (where n refers to the number of first columns), or even $n_1GC \times n_2GC$ (where $n_1$ refers to the number of the first columns and $n_2$ refers to the number of second columns).

Figure 5:
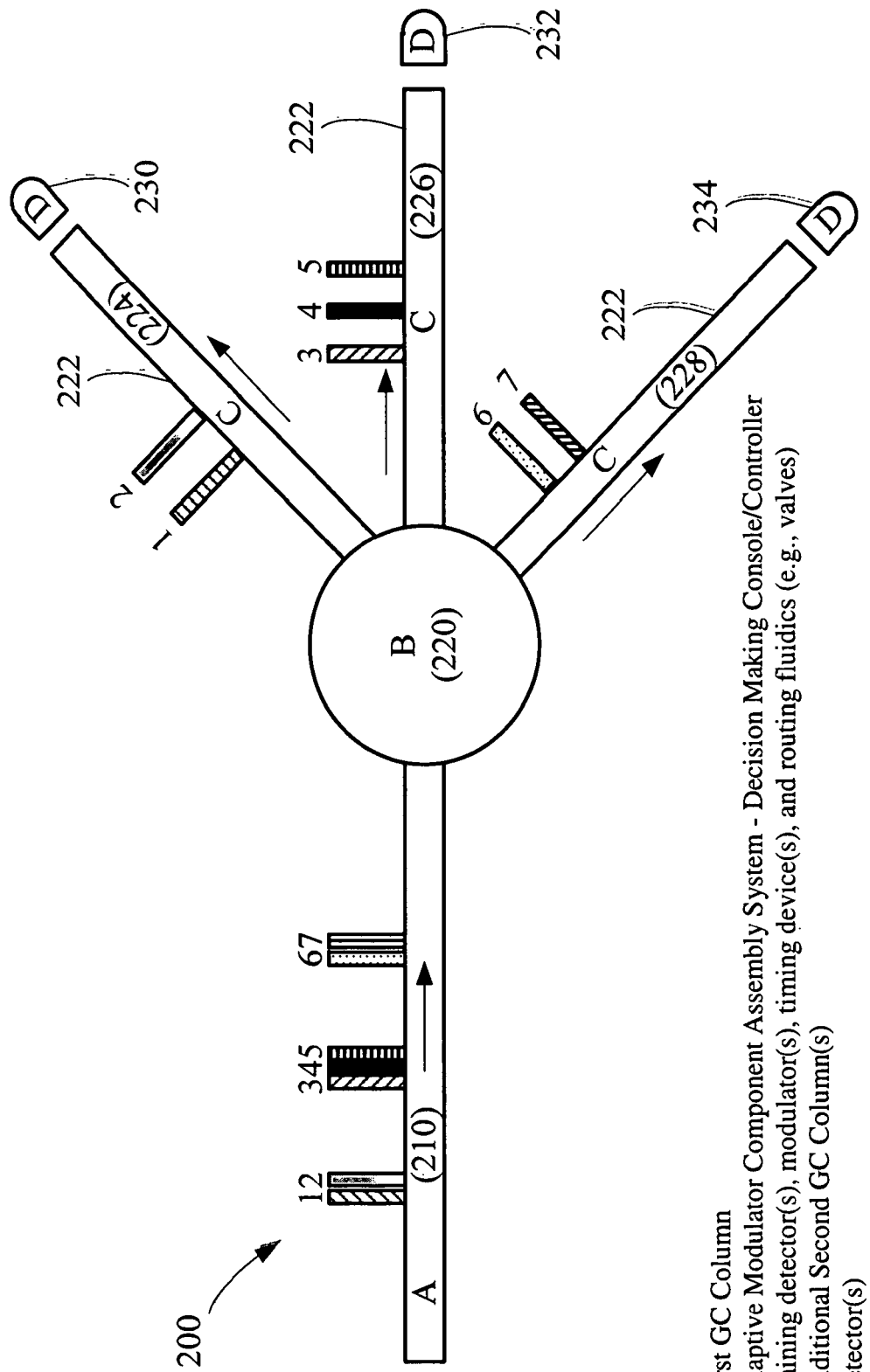
FIG. 5 shows a schematic of an alternative embodiment of an adaptive multi-dimensional micro-gas chromatography (μGC) device comprising GC×nGC columns (where n refers to the number of the second columns and is equal to 3).

Thus, in certain aspects, an adaptive micro-gas chromatography device 200 is provided in FIG. 5. The adaptive chromatography device 200 comprises a first micro-gas chromatographic column 210. The first micro-gas chromatographic column 210 receives a sample comprising one or more target analytes (designated by arrow "A"). The chromatography device 200 also comprises an adaptive modulator component assembly 220 disposed downstream of and in fluid communication with the first micro-gas chromatographic column. The modulator component assembly 220 comprises a first on-column detector (not shown) for detecting the presence of one or more target analytes eluted from the first micro-gas chromatographic column. The first on-column detector thus generates an output, to which the modulator component assembly 220 is responsive and thus controls flow. The modulator component assembly 220 thus regulates fluid flow into a plurality of downstream micro-gas chromatographic columns 222 in fluid communication therewith. The modulator component assembly 220 optionally further comprises one or more modulator devices, timing devices, and routing fluidics (e.g., valves and flow regulators), as appreciated by those of skill in the art. The modulator component assemblies according to various aspects of the present teachings provide an ability to adaptively regulate flow and efficiently operate micro-gas chromatography devices. In certain embodiments, described in more detail below, such modulator component assemblies may be automatically controlled via a control algorithm in a processor, such as a computer processing unit, to provide autonomous, independent operation of the adaptive micro-gas chromatography devices.

A plurality of downstream micro-gas chromatographic columns 222 is provided downstream from the modulator component assembly 220. Such downstream micro-gas chromatographic columns 222 may be provided in parallel to one another, or in alternative versions, in series to one another. As discussed in more detail below, the number of downstream chromatographic columns is not limited to one or two, but may include multiple downstream chromatographic columns. Where the plurality of downstream micro-gas chromatographic columns 222 is provided in parallel to one another, the modulator component assembly 220 has separate systems and components for controlling flow into each respective downstream micro-gas chromatographic column 222. The adaptive chromatographic device further comprises an additional detector for each respective downstream micro-gas chromatographic column so as to detect the presence of one or more target analytes eluted therefrom. The modulator component assembly 220 is thus responsive to an output generated by the first on-column detector so as to regulate fluid flow into the respective additional micro-gas chromatographic columns of the plurality of columns 222, in accordance with the operational principles discussed above.

In FIG. 5, the gas chromatography analytical device has GC×3GC (where GC×nGC has n=3) columns. The first chromatographic column 224 is labeled A. A sample comprising seven distinct target analytes (Nos. 1-7) is separated and the target analytes are eluted at different times. As can be seen, Analytes 1 and 2 are coeluted at a single peak, Analytes 3-5 are similarly coeluted at a single peak, and Analytes 6-7 are coeluted together. A modulator component assembly 220 in the form of a "decision making console" or controller is shown at B, which may include one or more detectors, including the detector for the first column (A), a thermal injector device, a timing device, and routing fluidics devices (such as valve(s)) (shown only generically as modulator component assembly 220). The modulator component assembly 220 regulates flow into the three additional distinct chromatographic columns 222 labeled C. The first chromatographic column is 224, the second chromatographic column is 226, and the third chromatographic column is 228. Each respective additional chromatographic column 222 has an additional detector 230 on first chromatographic column 224, detector 232 on second chromatographic column 226, and detector 234 on third chromatographic column 228 (each labeled as "D") at the terminal end of each respective downstream column 222. One chromatographic column 224 is selected to separate Analytes 1 and 2 from one another so that they are eluted at distinct peaks, another distinct column 226 is selected to separate Analytes 3-4 from one another so that they are eluted separately, and finally the last additional distinct column 228 separates Analytes 6 and 7 so that they are eluted as separate peaks. In a similar manner to that described previously above in the context of FIGS. 2A-2B, the modified 2-D GC design permits the modulator device 200 to adaptively regulate flow (here prevent flow) through the first column 210 into the additional columns 222 for a predetermined duration to permit processing in the additional columns. Such adaptive control is provided at least in part due to the modulator component assembly 220 being responsive to the output signal generated by detecting the presence of one or more target analytes in the first column 210.

Figure 6:
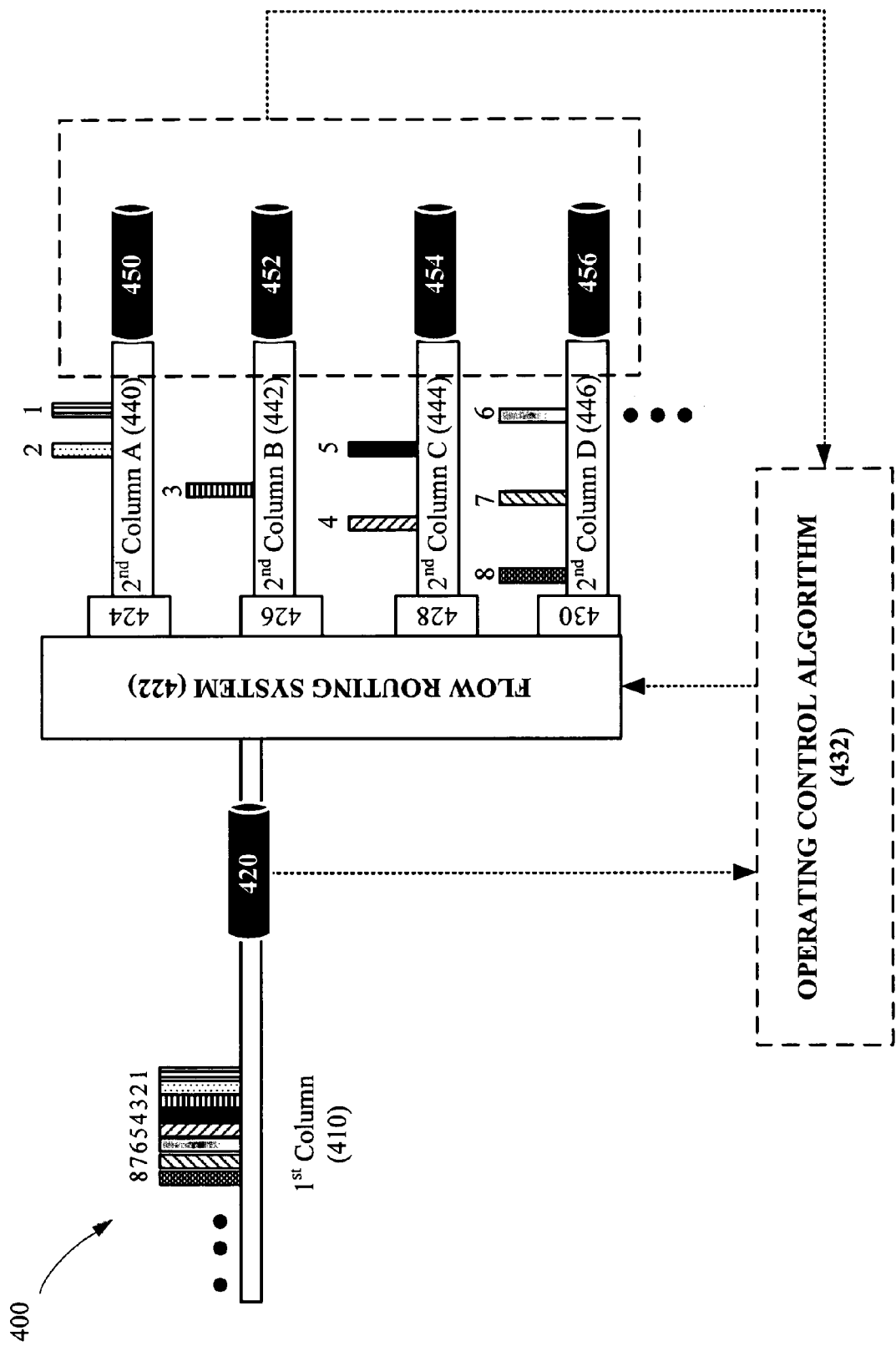
FIG. 6 shows an exemplary schematic of an alternative embodiment of an adaptive multi-dimensional micro-gas chromatography (μGC) device that is automated by a controller that has an operating control algorithm and further comprises GC×nGC columns (where n refers to the number of the second columns and is equal to 4).

In FIG. 6, another embodiment of a smart two-dimensional (2-D) micro-gas chromatography (μGC) architecture enables significant improvement for 2-D μGC performance. In this embodiment, a non-destructive on-column gas detector (first detector) and a flow routing system, such as a manifold assembly with actuatable valves and flow regulators, as well as controllable thermal injectors, are installed between the first dimensional separation column and multiple second dimensional separation columns. The eluent from the first dimensional column is monitored in real-time and a decision is then made by a control system to route the eluent to one or more of the second dimensional columns for further separation. Such an embodiment provides enhanced separation capability of the second dimensional column and hence the overall 2-D GC performance. All the second dimensional columns can be independently designed to have distinct properties from one another, including coatings, length, flow rate and temperature parameters that can be customized for optimizing separation results based on the target analytes to be detected or analyzed. In particular, there is no limit on the second dimensional column lengths and separation time in such embodiments prepared in accordance with certain aspects of the present technology, which differs from conventional 2-D GC systems. Such flexibility is important when long second dimensional separation is needed for optimal gas analysis. In addition, the smart μGC embodiments like those in FIG. 6 are advantageous in terms of elimination of the power intensive thermal modulator of conventional μGC systems, in that the thermal injector(s) are operated intermittently as needed, while providing higher peak amplitude enhancement, simplified 2-D chromatogram re-construction and scalability to higher dimensional separation. Furthermore, such a micro-gas chromatography system can be fully automated, for example, by using an algorithm for automated control/operation of a controller over the system.

More specifically, the smart multi-channel 2-D μGC system 400 shown in FIG. 6 includes the first column 410, an on-column first detector 420 installed at the end of the first column 410 to monitor the elution of a sample (having target analytes 1-8) from the first column 410. A flow routing system 422 controls connections between the first column 410 and a plurality of downstream second chromatographic columns, namely second column A 440, second column B 442, second column C 444, and second column D 446. Each of the second columns has its own thermal injector: namely injector A 424 on second column A 440, injector B 426 on second column B 442, injector C 428 on second column C 444, and injector D 430 on second column D 446. The injectors A-D (424, 426, 428 and 430) may be associated with the flow routing system 422, as a modulator component assembly like in the previously discussed embodiments. Each of the second columns A-D (440, 442, 444, and 446) also has its own on-column second detectors, namely second detector A 450 on second column A 440, second detector B 452 on second column B 442, second detector C 454 on second column C 444, and second detector D 456 on second column D 446. The on-column detectors 420, 450, 452, 454, and 456 are non-destructive and do not affect the flow or separation of samples/eluted samples in the system 400.

The smart multi-channel 2-D μGC system 400 also includes a fully automated control/operation algorithm 432. During analysis, the gas mixture sample is first separated at the first column 410 and the eluent that exits first column 410 is trapped by the thermal injectors A-D (424, 426, 428, and/or 430) after being routed through the flow routing system 422 to one of the second columns A-D (440, 442, 444, or 446). Such processes are monitored in real-time by the first detector 420. Once an entire eluent peak comes out of the first column 410 and is fully loaded onto one of the thermal injectors (424, 426, 428, and/or 430), the respective injector is triggered to inject the trapped eluent to the respective second column (either 440, 442, 444, or 446). This second column (440, 442, 444, or 446) is then registered as busy and is not assigned more eluent from the first column 410 by the operating control algorithm 432 until the separation is complete (or after certain predetermined time lapse). Meanwhile, the flow routing system 422 re-routes the subsequent eluent from the first column 410 to another available second column (440, 442, 444, or 446).

As compared to the conventional 2-D μGC systems, the smart 2-D μGC architecture provided by certain embodiments of the present teachings detects the eluents from the first column 410 and makes a decision via a controller to route the eluent to one of the second columns (440, 442, 444, or 446). Because of such a unique design, the smart 2-D μGC has several distinct advantages, including that (1) the entire eluent peak from the first column 410, (instead of a mere slice of it, as is the case for conventional 2-D μGC systems) is sent to one or more of the second columns 440, 442, 444, or 446 using a thermal injector (like 450, 452, 454, or 456). Consequently, the inventive μGC architecture according to certain aspects of the present teachings eliminates any need to use a high frequency thermal modulator, which is essential for conventional 2-D μGC. The repeated parsing of the first column eluent peak by a thermal modulator in a conventional system supposedly results in an increase in the peak capacity and sensitivity of 2-D GC analysis while retaining the original elute order upon the transition between the two columns. However, a careful analysis and comparison with 1-D GC indicates that real 2-D GC peak capacity cannot achieve the theoretical maximum $n_1 \times n_2$, where $n_1$ and $n_2$ are the peak capacity of the first and second columns under optimal stand-alone conditions, respectively. The compromise of 2-D GC is attributed primarily to peak broadening of the first column eluents during the re-construction of their original peak profile after the modulation process. However, in certain variations, the inventive adaptive chromatographic systems do not suffer from the shortcomings inherently accompanying the high-frequency operation of thermal modulator, thus significantly reducing the broadening effect caused by re-construction of the original peak profile and power consumption in the analysis.

Another advantage of certain variations of the present teachings is that each of the second columns downstream of the first column are independently designed, so that they can be preselected to have distinct coatings, length, flow rate and temperatures customized for achieving the best separation results (and can be tailored to best separate certain target analytes). In particular, there is no limit on the second column length (and separation time), as there is in conventional systems. Such flexibility is quite important when long second separation time is needed, thus significantly improving the secondary separation process that occurs in the second columns.

Yet another advantage of certain variations of the present teachings is that the entire analyte or sample (instead of just a slice of the sample or analyte) within an eluent peak is sent into the second column for separation. Thus, the peak amplitude enhancement (the ratio between the analyte peak from the first column and that from the second column) and hence the system detection limit are considerably improved, as compared to conventional designs. Furthermore, the μGC architecture is highly scalable. Higher dimensional separation (such as third and fourth separations) is contemplated, as well, which can be added by simply connecting additional columns to the outlet of the second columns. Further, because the on-column detectors record the retention time of each elution peak at the corresponding column in real-time, construction of 2-D (or even higher dimensional) chromatograms is greatly simplified.

Often target analytes present in a sample coexist or appear with clusters of other similar chemicals when sampled from an environment, although only detection of certain compounds within the cluster may be of interest. In this regard, the inventive technology can be used to efficiently detect certain compounds by searching for one or more known precursor compounds that frequently appear with target analytes of particular interest. Thus, certain precursor compounds may be known to appear or coexist with target analytes and may be more readily detectable. In certain aspects, a precursor component A may appear with target analytes B and C. Thus, if precursor component A is easily detected (has a distinctive peak when eluted from a particular chromatographic column), then the modulator component assembly may be activated to route the eluted sample into downstream chromatographic columns to determine whether target analytes B and C are indeed present in the sample. Such detection devices can be tailored based on libraries of information regarding specific chromatographic columns employed and behavior or target analytes and the precursor compounds or clusters with which they are associated. Thus, if the precursor compound(s) is/are eluted from the first chromatographic column within a certain time frame, the modulator component assembly can be activated for processing of the sample within one or more downstream chromatographic columns to further analyze the sample. However, if no precursor is detected as being eluted from the first chromatographic column, then the system can minimize power consumption by leaving the downstream chromatographic columns dormant. Such embodiments may be particularly useful in autonomous or remote monitoring systems, where minimizing power consumption can be particularly helpful. Furthermore, such systems and methods are highly customizable to numerous applications and for detection of various different target analytes.

Accordingly, in certain aspects, the present teachings provide a method of adaptive chromatography analysis that optionally comprises separating a sample in a first chromatographic column. An output signal may be generated by detecting one or more target analytes during or after the separating of the sample in the first chromatographic column. The method comprises adaptively regulating flow into at least one downstream chromatographic column based on the generated output signal to further separate the sample in the at least one downstream chromatographic column so as to analyze at least a portion of the one or more target analytes. The one or more target analytes may comprise a first target analyte and a second distinct target analyte. The first target analyte (or analytes) may be a species that appears or coexists with a second distinct target analyte (or analytes). Thus, the generating of the output signal can occur by detecting a first target analyte in the first chromatographic column, so that when the flow is adaptively regulated, at least a portion of the sample is directed or permitted to flow into the at least one downstream chromatographic column for detecting the second distinct target analyte.

Figure 8:
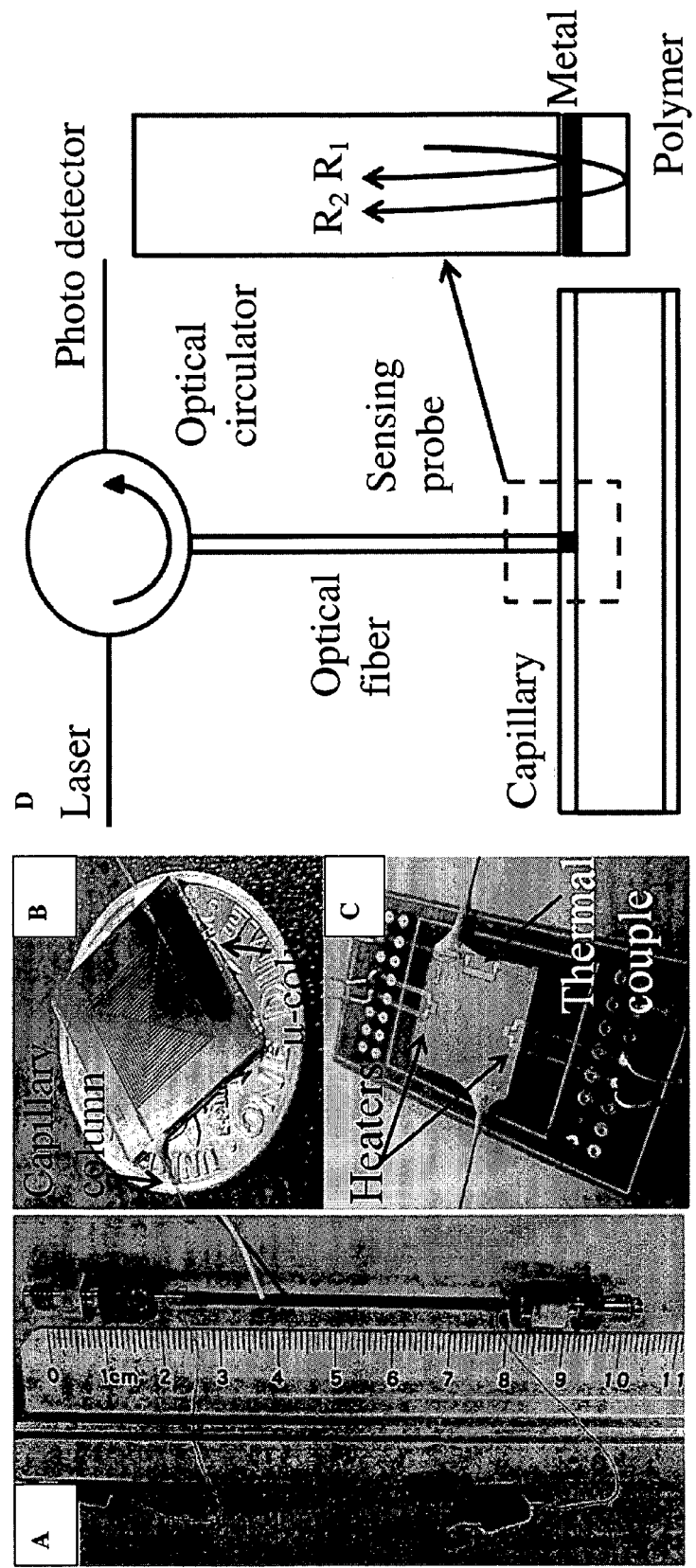

FIGS. 7 and 8A-8D show yet another embodiment of a smart multi-channel 2-D GC 300 according to certain aspects of the present teachings using conventional macro-scale components. The smart multi-channel 2-D μGC system 300 is automated. An optional preconcentrator 310 is provided before a first column 320 to concentrate the sample prior to separation. The preconcentrator 310 is a stainless steel tube (0.318 cm inner diameter (i.d.) packed with 2.1 mg of Carboxen 1018 micro-porous carbon beads, which are used as the adsorbent materials of the preconcentrator, are purchased from Supelco (Belafonte, Pa.) (specific area=675 m$^2$/g). The Carboxen 1018 beads are sieved to about 200 μm in diameter (60/80 mesh) held in place with a wire mesh and silanized glass wool (see FIG. 8A). The preconcentrator 310 is preconditioned initially at 300° C. for 24 hours under $N_2$. The preconcentrator 310 is then wrapped with an insulated copper heater wire (FIG. 8A) and thermally desorbed at 300° C. for 5 minutes, which serves to transfer the vapor mixture to the first column. As can be seen in FIG. 8A, a thermocouple is installed at the center of the preconcentrator 310 to monitor its temperature in real-time. The capacity of the preconcentrator 310 is verified in a separate series of tests, showing that the mass of each analyte trapped and transferred to the downstream GC matched that expected (within 1%).

First column 320 is a micro-fabricated column, which has an on-column gas first detector 322. The micro-fabricated column is fabricated by deep reactive ion etching a double spiral channel on a silicon substrate (see FIG. 8B). A Pyrex 7740 glass slide is bonded anodically to the silicon substrate to seal the channel from the top. The channel size shown in FIG. 8B is 240 μm by 150 μm. Two heaters and a thermocouple are embedded at the back of the chip for temperature ramping and monitoring, respectively (FIG. 8C).

The techniques and details for fabricating the on-column detector are discussed in Liu, Jing, et al., "Highly versatile fiber-based optical Fabry-Pérot gas sensor," *Optics Express*, Vol. 17, No. 4, pp. 2731-2738 (Feb. 16, 2009) (published online Feb. 10, 2009); Liu, Jing, et al., "Fabry-Pérot Cavity Sensors for Multipoint On-Column Micro Gas Chromatography Detection," *Analytical Chemistry*, Vol. 82, No. 11, pp. 4370-4375 (Jun. 1, 2010) (published online May 4, 2010); and Liu, Jing, et al., "Demonstration of motionless Knudsen pump based micro-gas chromatography featuring micro-fabricated columns and on-column detectors," *Lab Chip*, Vol. 11, pp. 3487-3492 (2011) (published online Aug. 25, 2011), previously incorporated by reference above. A layer of gold (thickness of 5 nm) and polydimethylsiloxane (PDMS) (thickness of 2 μm) is sequentially deposited on a sensing probe. Light coupled in the sensing probe is partially reflected at the gold layer and the interface between PDMS layer and air, generating a two beam interference spectrum. When the PDMS layer is exposed to gas analyte, its refractive index and/or thickness changes, resulting in the shift of the interference spectrum. By monitoring the interference spectrum shift, the quantitative and kinetic information of gas analytes is acquired. The sensing probe is then assembled with a short capillary column into an on-column detector, which can be easily connected to capillary separation columns through a universal quick seal column connector. An optical circulator is used to couple the light from a 1550 nm tunable diode laser into the sensing probe and redirect the reflected light into a photo detector (see schematic in FIG. 8D).

A flow routing system 328, which is an automated modulator assembly, includes three-way valves A and B 330, 332 and thermal injectors A and B 340, 342. Three-port valves (part no. 009-0269-900) are purchased from Parker (Cleveland, Ohio). Guard columns (part no. 10000, inner diameter=250 μm) are purchased from Restek (Bellefonte, Pa.). Universal quick seal column connectors (part no. 23627) and Universal angled "Y" connectors (part no. 20403-261) are purchased from Sigma and Restek, respectively.

A second column A 350 is connected to the thermal injector A 340 (contained within the flow routing system 328) and has a second detector A 360 at a terminal end. Likewise, a second column B 362 is connected to the thermal injector B 342 within the flow routing system 328 and has a second detector B 362 at a terminal end. Two different lengths of the second columns A 350 and B 360 are shown. Two different stationary phases of non-polar OV-1 and polar OV-215 are used to coat the micro-fabricated columns. The first column 320 is 1 meter long and is coated with OV-1. The second columns A and B 350, 352 are 0.5 m and 0.25 m long, respectively. Both are coated with OV-215. The coating procedures are as follows. First, OV-1 solution is prepared by dissolving 22.3 mg OV-1 and 0.2 mg dicumyl peroxide in a 6 mL mixture of 1:1 (v:v) pentane and dichloromethane, whereas OV-215 solution is prepared by dissolving 20 mg OV-215 and 0.2 mg dicumy peroxide in a 5 mL mixture of 1:4 (v:v) ether and ether acetate. Next, the micro-fabricated channel is filled with coating solution and held for 5 minutes. The coating solution is then evaporated from one end of the column by a vacuum pump, while the other end is sealed with a septum. The coating is cross-linked to the inner wall of the column by ramping the column temperature from 160° C. to 180° C. at a rate of 0.2° C./min and staying at 180° C. for one hour. The resultant column coating has a uniform thickness of around 200 nm.

Each thermal injector 340, 342 is made of a quartz tube (i.d.=2 mm, and 2 cm in length) packed with 6 mm long sorbent bed (Carbopack B and Tenax TA) held in place with silanized glass wool. Its outer surface is wrapped by an electrical coil for heating purposes. It is preconditioned at 300° C. under helium flow for one hour. The thermal injector can trap the eluent from the first column at room temperature and re-inject the trapped eluent onto the second column when heated up to 300° C. within three seconds.

Each of the second columns A and B 350, 352 are fluidly coupled to either gas pump A 370 or gas pump B 372 to facilitate flow of samples through the respective columns. Mini-diaphragm pumps (part no. D713-22-01) are purchased from Parker (Cleveland, Ohio). Further, while not shown, a control algorithm for control/operation of the system is used for automated operation of the various components, including of the flow routing system 328 in a similar manner to the embodiment generally described in FIG. 6.

A customized LabView™ program is developed for automated control and operation of the system, based upon characterization of the smart GC architecture using macro-scale components. The operation algorithm described herein is merely exemplary of one suitable for automation of the adaptive micro-gas chromatography devices, and may be modified to make the system more adaptive in control/operation, peak identification and trigger mechanism, by way of non-limiting example. The operation procedures can be divided into three steps. Step 1: includes the first column 320 connected (fluidly coupled) to second column A 350 and disconnected from second column B 352. The gas mixture is initially separated at first column 320 until first detector 322 detects a peak eluted out from first column 320. When the entire eluted peak passes first detector 322 and is trapped by thermal injector A 340 at second column A 350, a signal is generated to trigger three-port valve A 330 to disconnect second column A 350 from first column 320 and turn on thermal injector A 340 to inject the trapped analytes into second column A 350 for further separation. The system 300 then registers the status of second column A 350 as "busy." The "busy" status can be changed to "available" by a signal generated by second detector A 360 when second column A 350 completes separation or after certain pre-determined time lapse.

Step 2: occurs when three-port valve A 330 within flow routing system 328 disconnects second column A 350 from first column 320 during operation of Step 1, where second column B 352 is connected to first column 320. The remaining procedures are the same as those outlined above in Step 1.

Step 3: occurs when three-port valve B 332 disconnects second column B 352 from first column 320 during operation of Step 2. The system 300 inquires as to the status of second column A 350. If second column A 350 is "available," second column A 350 is reconnected to first column 320 and the procedures in Step 1 are repeated. If second column A 350 is "busy" (note that second column B 352 is "busy" at this moment), both second columns 350, 352 are disconnected from first column 320 and the separation at first column 320 is suspended, until one of the two second columns 350 or 352 becomes "available," at which time the separation at first column 320 resumes and the eluent is sent to this "available" second column (either 350 or 352).

Detailed calculation methods for the first and second retention times are discussed herein. The control/operation algorithm included two major modules: peak identification module and system control module. The peak identification module is implemented by using a Schmitt trigger coded in LabView™ to analyze the signal from the detector. Each detector in the smart 2-D μGC 300 (first detector 322, second detectors A and B 360, 362) has one Schmitt trigger attached. Two thresholds are set to the Schmitt trigger (see FIG. 9): a high threshold to identify the elution peak from noise and a low threshold to judge whether the peak has passed through the detector. When the vapor sensing signal from the detector exceeds the high threshold, the operation algorithm registers one elution peak to its respective detector and waits for the vapor sensing signal to fall below the low threshold. Once a pair of such vapor sensing signals is received, a "peak passed" signal is sent to the system control module.

The system control module controls the operation of flow routing system 328, including operation of the three-port valves A and B 330, 332, thermal injectors A and B 340, 342, and temperature ramping of first column 320. It is implemented by both software and hardware (see FIG. 10). The software control receives the "peak passed" signals from all detectors to decide which and when the trigger signal(s) are to be sent out. Each component listed above has one specific trigger signal to activate its corresponding hardware control. The activation of hardware by the trigger signal is controlled through a relay, which toggles the connection between this component and its power supply. When the trigger signal stays at a low voltage (0 V), the relay disconnects the component from the power supply. When the trigger signal sends a high voltage (5 V), the relay connects the component to the power supply.

The first and second retention times are calculated by the following equations (1) and (2): $1^{st}$ retention time=Elution time recorded by $1^{st}$ Detector−Total prior suspension time in the first column (1). $2^{nd}$ retention time=Elution time recorded by $2^{nd}$ Detector−The time when the separation at the corresponding second column started (i.e., when the thermal injector started to fire) (2). All the parameters in the above equations can be obtained directly from the real-time chromatograms from first and second detectors (e.g., 322, 360, 362). The separation shown in FIG. 12, as an example, is an enlarged part of FIG. 11A. The solid (dashed) boxes represent the separation duration at the first (second) column, while the spaces outside the solid (dashed) boxes represent the duration when the separation at the first (second) column is suspended. The separation at the first column 320 is suspended twice from 64 seconds to 71 seconds and from 143 seconds to 159 seconds, respectively. Consequently, the first retention time of analyte #15=210 s (elution time recorded by first detector 322)−23 s (total prior suspension time in the first column)=187 s. The $2^{nd}$ retention time of Analyte #15=240 s (elution time recorded by second detector A 360)−231 s (the time when the separation at second column A 350 starts)=9 s.

Such an automated two-dimensional (2-D) micro-gas chromatography device can be used to analyze various target analytes. In this example, thirty-one (31) workplace hazardous volatile organic compounds (VOCs) reported by California Standard Section 01350 Specification (February 2010 version 1.1) are tested. Further, rapid detection and identification of particular analytes out of interference background is demonstrated. All the analytes used in the experiment are purchased from Sigma (St. Louis, Mo.) and Fisher Scientific (Pittsburgh, Pa.). All analytes had purity greater than 97%.

The gas sample is prepared by mixing target gas analytes and inert nitrogen gas in a Tedlar bag (part no. 237-80, SKC Inc., Eighty Four, Pa.). The concentration of each gas analyte is listed in Table 1, which is the maximally allowable concentration reported by CA Section 01350. The prepared gas sample is sampled in a device similar to that in FIG. 7 by a preconcentrator through a six-port switching valve (not shown) under a high flow rate of 50 mL/min for 20 minutes. After sampling, the preconcentrator is heated up to 300° C. to release the sampled gas analytes by a back-flush flow. The mini-diagram pumps (e.g., 370, 372) installed at the end of the second columns (350, 352) deliver a flow rate of 1 mL/min. Ultra high purity helium is used as the carrier gas. The temperature profiles of the first and the second column and the thermal injectors are controlled by the LabView program (operating control algorithm) to provide automated operation. All other components are kept at room temperature.

The separation capability of a μGC system is affected by the factors such as stationary phase, column length, and temperature ramping, and the like. Optimization before actual analysis helps to ensure that the system is well-tuned to separate all components in the sample within a reasonably short amount of time. For the 2-D μGC according to certain aspects of the present teachings, the system separation capability is determined by the separation capability of both the first and the second columns. The optimal separation is achieved when analytes are sufficiently separated at both columns. In a conventional 2-D μGC system, optimization is usually accomplished through a trial-and-error process. In contrast, in certain variations of the inventive adaptive 2-D μGC systems, the on-column detectors provide important assessment of the separation capability of the first and the second columns.

To demonstrate this unique capability, a gas mixture containing six analytes (Analytes #15-#20 listed in Table 1) is used as the model system. More specifically, the target analytes are tetrachloroethylene, ethylbenzene, ethylene glycol, ethylene glycol monomethyl, ether chlorobenzene, and ethylene glycol monoethyl ether. First, a system with one first column (having a length of 25 cm) and two second columns of 50 cm and 25 cm length, respectively, is used. FIG. 13A shows the real-time chromatograms obtained from this configuration. Apparently, significant coelution occurred at first column. Because a trigger signal is designed to be generated near the baseline, the entire coeluted analytes (all six analytes in this particular case) are sent to second column A, resulting in insufficient separation of those analytes.

The chromatograms provided by first detector and second detector A suggest that the above failure is due primarily to the insufficient separation of the analytes in the first column. Once the cause of failure has been identified, a number of methods are readily available to address this problem, such as changing the first column length, the second column length, the flow rate, or the temperature ramping profile. As one non-limiting way of addressing this issue, the length of the first column was increased to 1 meter, while keeping all other settings unchanged. As shown in FIG. 13B, the gas mixture is separated into two (yet still coeluted) peaks in the first column and all six analytes could be completely separated after the second columns. It should be emphasized that in contrast to adaptive 2-D μGC systems prepared in accordance with certain aspects of the present teachings, such optimization is difficult to implement with conventional 2-D μGC, as it is difficult to determine whether the insufficient 2-D separation is caused by the insufficient separation at the first column, the second column, or both.

After optimization of the 2-D μGC system in the same manner as described above, 31 workplace hazardous VOCs reported by California Standard Section 01350 Specification (February 2010 version 1.1), which is the most popular U.S. standard for evaluating and restricting indoor VOC emissions, are analyzed. The name and the maximally allowable concentration of each analyte are listed in Table 1.

TABLE 1

List of 31 workplace hazardous VOCs and their maximally allowable concentrations

| No. | Analyte Name/Compound | Maximally Allowable Concentration (ng/L) |
|---|---|---|
| 1 | Carbon disulfide | 400 |
| 2 | Dichloroethylene | 35 |
| 3 | Methyl t-butyl ether | 4000 |
| 4 | Acetaldehyde | 70 |
| 5 | Methylene chloride | 200 |
| 6 | Chloroform | 150 |
| 7 | Hexane | 3500 |
| 8 | Dimethylformamide | 40 |
| 9 | Benzene | 30 |
| 10 | Carbon tetrachloride | 20 |
| 11 | Trichloroethylene | 300 |
| 12 | Dioxane | 1500 |
| 13 | Toluene | 150 |
| 14 | Vinyl acetate | 100 |
| 15 | Tetrachloroethylene | 17.5 |
| 16 | Ethylbenzene | 1000 |
| 17 | Ethylene glycol | 200 |
| 18 | Ethylene glycol monomethyl ether | 30 |
| 19 | Chlorobenzene | 500 |
| 20 | Ethylene glycol monoethyl ether | 35 |
| 21 | Isopropanol | 3500 |
| 22 | Methyl chloroform | 500 |
| 23 | Styrene | 450 |
| 24 | m-Xylene | 350 |
| 25 | Ethylene glycol monomethyl ether acetate | 45 |
| 26 | Propylene glycol monomethyl ether | 3500 |
| 27 | Formaldehyde | 16.5 |
| 28 | Ethylene glycol monoethyl ether acetate | 150 |
| 29 | Phenol | 100 |
| 30 | Dichlorobenzene | 400 |
| 31 | Isophorone | 1000 |

The first analysis is conducted under isothermal condition at room temperature. As shown in FIG. 11A, three real-time chromatograms are obtained from first detector, second detector A and B, respectively. At first column, 31 analytes are separated into 12 baseline-separated peaks, which are then sent to second column A and B, alternately for further separation. Total analysis is completed within 38 minutes. FIG. 11B is the extracted 2-D chromatogram, from which a wide range of the retention time at the second column is observed up to approximately 4 minutes. Such long second dimensional retention time would pose a significant challenge for a conventional 2-D μGC system due to the wrap-around issue, whose maximal second column separation time is limited by the modulation period (ranging from sub-second to a few seconds).

To accelerate the analysis, temperature ramping is applied in this example. The first column is initially kept at 35° C. until the elution of the $11^{th}$ peak at the first column, which is then heated up to 100° C. in 3 minutes. Both second columns are kept at 45° C. during the whole analysis. FIG. 14A plots the three chromatograms from the first and two second columns. Total analysis time is shortened to 20 min. FIG. 14B shows the extracted 2-D chromatogram. The longest second dimensional retention time is approximately 110 seconds, which would still be too difficult to handle with the conventional 2-D μGC system.

In many applications, detection and identification of a particular target gas analyte or a set of analytes from interference background in a short time is of greatest interest. In such embodiments, a complete separation of all components in a gas mixture may not be necessary. Rather, only the target analytes need to be separated out, which can greatly simplify the analysis procedures and shorten the analysis time.

To demonstrate such versatility of an automated two-dimensional (2-D) micro-gas chromatography device according to certain variations of the present teachings, the same 31 VOCs are used, among which toluene and phenol are used as the target analytes and the remaining 29 VOCs served as interference background. The system configuration is the same as used in FIG. 13B. According to FIG. 13B, the first and second dimensional retention time of toluene (phenol) is 130 (753) seconds and 16 (92) seconds, respectively. Therefore, modifications are made in the LabView codes to define two time windows from 126 seconds to 136 seconds and from 720 seconds to 820 seconds, respectively, at the first dimension. If an eluent peak is detected within these two windows, the peak will be then sent to the second Column B for further separation/analysis. Any eluents outside these two windows are simply vented through second Column A without conducting any further analysis. Note that the window at the first dimension can be very narrow (narrower than the elution peak) to ensure that most of the target analyte (eluted sample) is sent to the second column while significantly rejecting interference background (even though they may coelute with the target analyte). Therefore, the second column separation becomes even easier, as fewer interferents are mixed in. At the second dimension, the second Detector B identifies the peaks that have the same second retention times as the target analytes.

As shown in FIG. 15, the first detector detected an eluent peak within the first time window, which is sent to second column B for further separation. The second detector B then identified a peak that has the same second retention time as toluene, indicating that toluene is contained in the gas mixture. Meanwhile, when the eluent in the first time window is analyzed at second column B, the separation at the first column continues without interruption. The first detector then detected another eluent peak within the second time window, which is again sent to second column B for detection of phenol. Since no separation and analysis are conducted at second column A, the signal of second detector A is not present.

This detection and identification scenario is especially attractive for power consumptive applications, such as remote autonomous monitoring, because it reduces the number of modulations for each analysis (no more than the number of the target analytes). When applied in the remote autonomous monitoring application, the system can be placed in the stand-by mode, only awakened by a suspicious peak(s) detected within the pre-determined window(s) at the first column.

As such, in various aspects, the smart adaptive µGC prepared in accordance with certain aspects of the present disclosure can be used as a general-purpose gas analysis instrument having significantly enhanced second dimensional separation capability unattained with the conventional 2-D µGC. Further, the inventive technology can be adapted for particular applications where only a set of target analytes need to be detected. For example, in certain applications and industries, only certain target analytes are of interest, for example, specific pesticides, toxins or poisonous compounds, or explosive compounds, by way of non-limiting examples. Thus, the inventive adaptive gas chromatography devices may be employed in various detection apparatuses and systems. Because the adaptive modulator component assembly provides efficient, reduced-power consumption as compared to conventional GC systems, and furthermore provides high accuracy in detection and potentially automated operation, such devices can be used in remote surveillance and autonomous monitoring equipment for various environments. Accordingly, the inventive technology is highly flexible and can be tailored to specific applications, and thus, can be readily adapted for particular applications where only a limited set of target analytes need to be detected or analyzed.

Accordingly, therefore, in accordance with certain aspects of the present disclosure, methods for conducting chromatography analysis provide the ability to efficiently regulate and adaptively control flow of a sample into one or more downstream chromatographic columns, based upon detecting changes in one or more upstream conditions, such as the presence of one or more target analytes in the sample, temperature, pressure, gas flow velocity, and combinations thereof. Therefore, in certain variations, adaptive micro-gas chromatography (micro-GC) systems are contemplated that comprise an adaptive modulator component assembly that is reactive to changes in one or more system conditions, so as to provide higher separation speed, better analyte identification capability, and higher savings in power consumption than in conventional micro-GC devices. Such adaptive micro-gas chromatography (micro-GC) systems may be fully automated during operation.

Specifically disclosed are embodiments of an adaptive chromatography device, comprising: a first chromatographic column that receives a sample comprising one or more target analytes; and a modulator component assembly disposed downstream of and in fluid communication with the first chromatographic column. The modulator component assembly comprises a first detector for detecting the presence of one or more target analytes eluted from the first chromatographic column and a thermal injector device. A second chromatographic column is disposed downstream of and in fluid communication with the modulator component assembly. A second detector for detecting the presence of one or more target analytes eluted from the second chromatographic column is also provided as part of the adaptive chromatography device. The modulator component assembly is responsive to an output generated by the first detector to regulate fluid flow into the second chromatographic column. The adaptive chromatography device optionally has any one or any combination of more than one of the following features: (1) that the modulator component assembly further comprises a valve, wherein in a first position, the valve permits fluid to flow from the first chromatographic column into the second chromatographic column and in a second position, the valve prevents fluid from flowing from the first chromatographic column into the second chromatographic column, wherein the output from the first detector is capable of changing the valve from the first position to the second position; (2) where the valve is a three-way valve and in the second position the valve receives a supplemental carrier fluid that flows with the sample into the second chromatographic column; (3) that the modulator component assembly is automatically controlled by an automated controller; (4) further comprising at least one additional chromatographic column disposed downstream from and in fluid communication with the modulator component assembly. The modulator component assembly also regulates fluid flow from the first chromatographic column into the at least one additional chromatographic column based on the output generated by the first detector; (5) the first detector is a non-destructive on-column detector selected from the group consisting of: a capillary based optical ring resonator (CBORR)

device, a Fabry-Pérot interferometer based sensor, a chemi-resistor sensor, a sound acoustic wave sensor, and a thermal conductivity sensor; (6) the output generated by the first detector is a first output and a second output is generated by the second detector, where the modulator component assembly is responsive to both the first output and the second output to regulate fluid flow in both the first chromatographic column and the second chromatographic column; (7) the first chromatographic column is a first micro-gas chromatographic column and the second chromatographic column is a second micro-gas chromatographic column; (8) further comprising at least one additional micro-gas chromatographic column downstream from and in fluid communication with the modulator component assembly, where the modulator component assembly also regulates fluid flow into the at least one additional micro-gas chromatographic column; where the at least one additional micro-gas chromatographic column is configured in series with the second micro-gas chromatographic column downstream from and in fluid communication with the modulator component assembly, and the modulator component assembly selectively controls fluid flow into the second micro-gas chromatographic column or the at least one additional micro-gas chromatographic column based on the output generated by the first detector, where these features include any combinations of those disclosed that may be included in devices mentioned for these features.

All possible combinations discussed and enumerated above as optional features of these devices are specifically disclosed as embodiments. Also specifically disclosed are combinations including the adaptive chromatography optionally with any one or any combination of more than one of the enumerated features (1)-(8).

In yet other aspects, the present disclosure contemplates embodiments of an adaptive micro-gas chromatography device, comprising a first micro-gas chromatographic column. The first micro-gas chromatographic column receives a sample comprising one or more target analytes. The adaptive micro-gas chromatography device comprises a modulator component assembly disposed downstream of and in fluid communication with the first chromatographic column. The modulator component assembly comprises a first on-column detector for detecting the presence of one or more target analytes eluted from the first micro-gas chromatographic column and a thermal injector device. The adaptive micro-gas chromatography device also comprises a second micro-gas chromatographic column comprising a second detector for detecting the presence of one or more target analytes eluted from the second micro-gas chromatographic column. The second micro-gas chromatographic column is disposed downstream of and in fluid communication with the modulator component assembly, where the modulator component assembly is responsive to an output generated by the first on-column detector to regulate fluid flow into the second micro-gas chromatographic column. The adaptive micro-gas chromatography device optionally has any one or any combination of more than one of the following features: (1) the modulator component assembly further comprises a valve, where in a first position, the valve permits fluid to flow from the first micro-gas chromatographic column into the second micro-gas chromatographic column and in a second position, the valve prevents fluid from flowing from the first micro-gas chromatographic column into the second micro-gas chromatographic column. Further, the output from the first on-column detector is capable of changing the valve from the first position to the second position; (2) the valve is a three-way valve and in the second position the valve receives a supplemental carrier fluid that flows with the sample into the modulator component assembly and then the second chromatographic column; (3) further comprising at least one additional micro-gas chromatographic column downstream from and in fluid communication with the modulator component assembly, where the modulator component assembly also regulates fluid flow into the at least one additional micro-gas chromatographic column; (4) the first on-column detector is a non-destructive detector selected from the group consisting of: a capillary based optical ring resonator (CBORR) device, a Fabry-Pérot interferometer based sensor, a chemi-resistor sensor, a sound acoustic wave sensor, and a thermal conductivity sensor; (5) the output generated by the first on-column detector is a first output and a second output is generated by the second detector, where the modulator component assembly is responsive to both the first output and the second output to regulate fluid flow in both the first micro-gas chromatographic column and the second micro-gas chromatographic column, where these features include any combinations of those disclosed that may be included in devices mentioned for these features.

All possible combinations discussed and enumerated above as optional features of these devices are specifically disclosed as embodiments. Also specifically disclosed are combinations including the adaptive micro-gas chromatography devices optionally with any one or any combination of more than one of the enumerated features (1)-(5).

In yet other embodiments, an adaptive micro-gas chromatography device comprises a first micro-gas chromatographic column that receives a sample comprising one or more target analytes, a modulator component assembly disposed downstream of and in fluid communication with the first micro-gas chromatographic column, which regulates fluid flow into a plurality of downstream micro-gas chromatographic columns in fluid communication therewith. The modulator component assembly comprises a first on-column detector and a thermal injector device. The first on-column detector detects the presence of one or more target analytes eluted from the first micro-gas chromatographic column that generates an output. The device further comprises an additional detector for each respective downstream micro-gas chromatographic column so as to detect the presence of one or more target analytes eluted therefrom. The modulator component assembly is responsive to an output generated by the first on-column detector to regulate fluid flow into the respective downstream micro-gas chromatographic columns. The adaptive micro-gas chromatography device optionally has any one or any combination of more than one of the following features: (1) the first on-column detector is a non-destructive detector selected from the group consisting of: a capillary based optical ring resonator (CBORR) device, a Fabry-Pérot interferometer based sensor, a chemi-resistor sensor, a sound acoustic wave sensor, and a thermal conductivity sensor; (2) the modulator component further comprises a valve disposed between the first micro-gas chromatographic column and the second micro-gas chromatographic column, where in a first position, the valve permits fluid to flow from the first micro-gas chromatographic column into the second micro-gas chromatographic column and in a second position, the valve prevents fluid from flowing from the first micro-gas chromatographic column into the second micro-gas chromatographic column. Moreover, the output from the first on-column detector is capable of changing the valve from the first position to the second position; (3) the output generated by the first on-column detector is a first output and a second output is generated by the second detector, where the modulator component assembly is responsive to both the first output and the second output to regulate fluid flow in both the first micro-gas chromatographic column and the second micro-gas chromatographic column.

All possible combinations discussed and enumerated above as optional features of these devices are specifically disclosed as embodiments. Also specifically disclosed are combinations including the adaptive micro-gas chromatography devices optionally with any one or any combination of more than one of the enumerated features (1)-(4).

In certain variations, a method for conducting adaptive chromatography analysis may comprise separating a sample in a first chromatographic column to generate one or more eluted target analytes, followed by introducing the one or more eluted target analytes into at least one downstream chromatographic column for a second separation of the one or more eluted target analytes. The one or more system conditions are detected upstream of the at least one downstream chromatographic column for regulating flow into the at least one downstream chromatographic column. The one or more system conditions may be selected from the group consisting of: presence of one or more target analytes in the sample, temperature, pressure, gas flow velocity, and combinations thereof.

In other variations, the present disclosure provides methods for conducting adaptive chromatography analysis, which may comprise separating a sample in a first chromatographic column, followed by generating an output by detecting one or more target analytes during or after the separating of the sample in the first chromatographic column. Flow is adaptively regulated into at least one downstream chromatographic column based on the generated output to further separate the sample in the at least one downstream chromatographic column so as to analyze at least a portion of the one or more target analytes. The method for conducting adaptive gas chromatography analysis optionally has any one or any combination of more than one of the following additional steps or features: (1) one or more system conditions may be detected upstream of the downstream chromatographic column and changes in one or more system conditions may be used to generate the output and thus regulate flow into the downstream chromatographic column; (2) where one or more system conditions that are detected are selected from the group consisting of: presence of one or more target analytes in the sample, temperature, pressure, gas flow velocity, and combinations thereof; (3) a sample is separated in a first chromatographic column and after elution from the first chromatographic column, the sample is introduced into a modulator component assembly that detects one or more target analytes in the sample after elution from the first chromatographic column so as to generate an output signal in the presence of the one or more target analytes and that regulates flow of the sample into a second downstream chromatographic column, and further separating the sample in the second chromatographic column and further detecting the one or more target analytes eluted from the second chromatographic column. The modulator component assembly adaptively regulates flow of the sample into the second micro-gas chromatographic column based on the output signal; (4) where during the detecting, a baseline output signal is generated in the absence of the one or more target analytes and a peak output signal is generated in the presence of the one or more target analytes, so that after the output signal reaches the peak output signal and falls to the baseline output signal, the modulator component assembly inhibits the flow of the sample from the first chromatographic column into the second chromatographic column for a predetermined period to permit the sample to pass through the second chromatographic column; (5) where after the sample passes through and is eluted from the second chromatographic column and the further detecting of the one or more target analytes indicates that separating and eluting the sample is completed in the second chromatographic column, a second output signal is generated that is received by the modulator component assembly that is responsive to the second output signal and restores flow through the first chromatographic column; (6) where a carrier gas is supplied to the modulator component assembly to flow with the sample into the second chromatographic column during the predetermined period; (7) the modulator component assembly further comprises a three-way valve, wherein in a first position, the three-way valve permits the sample to flow from the first chromatographic column into the second chromatographic column and in a second position, the three-way valve prevents the sample from flowing from the first chromatographic column into the second chromatographic column, but permits the carrier gas to enter the second chromatographic column, wherein the output signal is capable of changing the valve from the first position to the second position; (8) the modulator component assembly traps and refocuses the eluted sample, so that when the output signal falls from the peak output signal to the baseline output signal, the trapped eluted sample is rapidly heated in the modulator component assembly and injected into the second chromatographic column; (9) wherein the generating of the output signal by detecting one or more target analytes and the adaptively regulating flow are automatically controlled by a processor; and/or (10) where the one or more target analytes comprise a first target analyte and a second distinct target analyte. The generating of the output signal occurs by detecting a first target analyte in the first chromatographic column, so that the adaptively regulating flow permits or directs at least a portion of the sample to flow into the at least one downstream chromatographic column for detecting the second distinct target analyte.

All possible combinations discussed and enumerated above as optional features of these methods are specifically disclosed as embodiments. Also specifically disclosed are combinations including the methods for conducting adaptive chromatography analysis optionally with any one or any combination of more than one of the enumerated steps or features (1)-(10).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An adaptive chromatography device, comprising:
a first chromatographic column that receives a sample comprising one or more target analytes;
a modulator component assembly disposed downstream of and in fluid communication with the first chromatographic column, wherein the modulator component assembly comprises:
a first detector for detecting the presence of one or more target analytes eluted from the first chromatographic column and a thermal injector device; and
a valve, wherein in a first position, the valve permits fluid to flow from the first chromatographic column into the second chromatographic column and in a second position, the valve prevents fluid from flowing from the first chromatographic column into the second chromatographic column, wherein the output generated by the first detector is capable of changing the valve from the first position to the second position;

a second chromatographic column disposed downstream of and in fluid communication with the modulator component assembly; and a second detector for detecting the presence of one or more target analytes eluted from the second chromatographic column; wherein the modulator component assembly is responsive to an output generated by the first detector to regulate fluid flow into the second chromatographic column.

2. The adaptive chromatography device of claim 1, wherein the valve is a three-way valve and in the second position the valve receives a supplemental carrier fluid that flows with the sample into the second chromatographic column.

3. The adaptive chromatography device of claim 1, further comprising at least one additional chromatographic column disposed downstream from and in fluid communication with the modulator component assembly and the first chromatographic column, wherein the modulator component assembly also regulates fluid flow from the first chromatographic column into the at least one additional chromatographic column based on the output generated by the first detector.

4. The adaptive chromatography device of claim 1, wherein the first detector is a non-destructive on-column detector selected from the group consisting of: a capillary based optical ring resonator (CBORR) device, a Fabry-Perot interferometer based sensor, a chemi-resistor sensor, a sound acoustic wave sensor, and a thermal conductivity sensor.

5. The adaptive chromatography device of claim 1, wherein the output generated by the first detector is a first output and a second output is generated by the second detector, wherein the modulator component assembly is responsive to both the first output and the second output to regulate fluid flow in both the first chromatographic column and the second chromatographic column.

6. The adaptive chromatography device of claim 1, wherein the first chromatographic column is a first micro-gas chromatographic column and the second chromatographic column is a second micro-gas chromatographic column.

7. The adaptive chromatography device of claim 6, further comprising at least one additional micro-gas chromatographic column downstream from and in fluid communication with the modulator component assembly, wherein the modulator component assembly also regulates fluid flow into the at least one additional micro-gas chromatographic column.

8. The adaptive chromatography device of claim 7, wherein the at least one additional micro-gas chromatographic column is configured in series with the second micro-gas chromatographic column downstream from and in fluid communication with the modulator component assembly, and the modulator component assembly selectively controls fluid flow into the second micro-gas chromatographic column or the at least one additional micro-gas chromatographic column based on the output generated by the first detector.

9. An adaptive micro-gas chromatography device, comprising:

a first micro-gas chromatographic column, wherein the first micro-gas chromatographic column receives a sample comprising one or more target analytes; and a modulator component assembly disposed downstream of and in fluid communication with the first micro-gas chromatographic column, which regulates fluid flow into a plurality of downstream micro-gas chromatographic columns in fluid communication therewith, wherein the modulator component assembly comprises:

a first on-column detector for detecting the presence of one or more target analytes eluted from the first micro-gas chromatographic column and a thermal injector device, wherein the adaptive micro-gas chromatography device further comprises an additional detector for each respective downstream micro-gas chromatographic column so as to detect the presence of one or more target analytes eluted therefrom; wherein the first on-column detector generates an output received by the modulator component assembly to regulate fluid flow into the respective downstream micro-gas chromatographic columns; and a flow regulating device disposed between the first micro-gas chromatographic column and the plurality of downstream micro-gas chromatographic columns, wherein in a first position, the flow regulating device permits fluid to flow from the first micro-gas chromatographic column into at least one of the plurality of downstream micro-gas chromatographic columns and in a second position, the flow regulating device prevents fluid from flowing from the first micro-gas chromatographic column into at least one of the plurality of downstream micro-gas chromatographic columns, wherein the output from the first on-column detector is capable of changing the flow regulating device from the first position to the second position.

10. The adaptive micro-gas chromatography device of claim 9, wherein the first on-column detector is a non-destructive detector selected from the group consisting of: a capillary based optical ring resonator (CBORR) device, a Fabry-Perot interferometer based sensor, a chemi-resistor sensor, a sound acoustic wave sensor, and a thermal conductivity sensor.

11. The adaptive micro-gas chromatography device of claim 10, wherein the output generated by the first on-column detector is a first output and at least one additional output is generated by at least one of the additional detectors of the plurality of downstream micro-gas chromatographic columns, wherein the modulator component assembly is responsive to both the first output and the at least one additional output to regulate fluid flow in both the first micro-gas chromatographic column and the plurality of downstream micro-gas chromatographic columns.

12. A method of adaptive chromatography analysis comprising:

separating a sample in a first chromatographic column;

generating an output signal by detecting one or more target analytes during or after the separating of the sample in the first chromatographic column;

adaptively regulating flow into at least one downstream chromatographic column based on the generated output signal to further separate the sample in the at least one downstream chromatographic column so as to analyze at least a portion of the one or more target analytes; and generating a baseline output signal in the absence of the one or more target analytes in the first chromatographic column and further generating a peak output signal in the presence of the one or more target analytes in the first chromatographic column, so that after the generated output signal reaches the peak output signal and falls to the baseline output signal, flow between the first chromatographic column into the at least one downstream chromatographic column is inhibited for a predetermined period to permit the sample to pass through the at least one downstream chromatographic column.

13. The method of claim 12, wherein after the sample passes through and is eluted from the at least one downstream chromatographic column, a second output signal is generated by the at least one downstream chromatographic column to restore fluid flow through the first chromatographic column.

14. The method of claim 13, wherein a carrier gas is injected downstream of the first chromatographic column to flow with the sample into the at least one downstream chromatographic column during the predetermined period.

15. The method of claim 14, wherein a modulator component assembly comprises a three-way valve disposed between the first chromatographic column and the at least one downstream chromatographic column, wherein in a first position, the three-way valve permits the sample to flow from the first chromatographic column into the at least one downstream chromatographic column and in a second position, the three-way valve prevents the sample from flowing from the first chromatographic column into the at least one downstream chromatographic column, but permits the carrier gas to enter the at least one downstream chromatographic column, wherein the output signal is capable of changing the three-way valve from the first position to the second position.

16. The method of claim 15, wherein the modulator component assembly traps and re-focuses the eluted sample from the first chromatographic column, so that when the generated output signal falls from the peak output signal to the baseline output signal, the trapped eluted sample is rapidly heated in the modulator component assembly and injected into the at least one downstream chromatographic column.

17. The method of claim 15, wherein the generating of the output signal by detecting one or more target analytes and the adaptively regulating flow are automatically controlled by a processor.

18. The method of claim 12, wherein the one or more target analytes comprises a first target analyte and a second distinct target analyte, wherein the generating of the output signal occurs by detecting the first target analyte in the first chromatographic column, so that the adaptively regulating flow permits at least a portion of the sample to flow into the at least one downstream chromatographic column for detecting the second distinct target analyte.

19. An adaptive micro-gas chromatography device, comprising:
 a first micro-gas chromatographic column, wherein the first micro-gas chromatographic column receives a sample comprising one or more target analytes; and
 a modulator component assembly disposed downstream of and in fluid communication with the first micro-gas chromatographic column, which regulates fluid flow into a plurality of downstream micro-gas chromatographic columns in fluid communication therewith, the plurality of downstream micro-gas chromatographic columns in provided in parallel to one another, wherein the modulator component assembly comprises a first on-column detector for detecting the presence of one or more target analytes eluted from the first micro-gas chromatographic column and a thermal injector device, wherein the adaptive micro-gas chromatography device further comprises an additional detector for each respective downstream micro-gas chromatographic column so as to detect the presence of one or more target analytes eluted therefrom; wherein the first on-column detector generates an output received by the modulator component assembly to regulate fluid flow into the respective downstream micro-gas chromatographic columns.

* * * * *